(12) United States Patent
Haroutunian

(10) Patent No.: US 9,155,849 B2
(45) Date of Patent: *Oct. 13, 2015

(54) FLOW MODIFICATION DEVICE

(71) Applicant: G Greg Haroutunian, Beverly Hills, CA (US)

(72) Inventor: G Greg Haroutunian, Beverly Hills, CA (US)

(*) Notice: Subject to any disclaimer, the term of this patent is extended or adjusted under 35 U.S.C. 154(b) by 254 days.

This patent is subject to a terminal disclaimer.

(21) Appl. No.: 13/765,692

(22) Filed: Feb. 12, 2013

(65) Prior Publication Data

US 2014/0048065 A1 Feb. 20, 2014

Related U.S. Application Data

(63) Continuation-in-part of application No. 11/975,592, filed on Oct. 19, 2007, now Pat. No. 8,371,291.

(60) Provisional application No. 60/853,347, filed on Oct. 19, 2006.

(51) Int. Cl.
*B05B 1/26* (2006.01)
*A61M 15/00* (2006.01)
(Continued)

(52) U.S. Cl.
CPC .......... *A61M 15/0065* (2013.01); *A61M 15/009* (2013.01); *A61M 15/0021* (2014.02);
(Continued)

(58) Field of Classification Search
CPC ........... G01M 9/00; G01M 9/02; G01M 9/04; G01M 9/065; F15D 1/0005; F15D 1/001; F15D 1/02; F15D 1/04; F15D 1/06; F15D 1/065; F15D 1/10; F15D 1/12; F15D 1/14; A61M 2206/11; A61M 11/003; A61M 15/0086; A61M 15/002

USPC ........... 138/37, 39, 40, 44, 94; 131/199, 210, 131/216, 339, 344; 128/200.18
See application file for complete search history.

(56) References Cited

U.S. PATENT DOCUMENTS 2,906,463 A 9/1959 Curry
3,453,811 A 7/1969 Crowley
(Continued)

FOREIGN PATENT DOCUMENTS

JP 2003-37383 2/2003

OTHER PUBLICATIONS

W.J. Prest, W. F. Raymond, Fractal Magnetism: Structure and 4D Winding, Syzygy Desktop Publications; Mar. 2004; http://geocities.com/syzygywjp/FractalMagneticField.html. pp. 1-4.
(Continued)

*Primary Examiner* — Lynne Anderson
*Assistant Examiner* — Peter S Vasat
(74) *Attorney, Agent, or Firm* — Thorpe North & Western, LLP

(57) ABSTRACT

A basic air flow device includes a flow passage having opposite ends. The flow passage is divided into a plurality of sequential portions between the ends including an inlet portion extending into the flow passage from an inlet end, an outlet portion disposed at the opposite end of the flow passage from the inlet portion, and at least one intermediate passage portion between the inlet passage portion and the outlet passage portion. Each of a plurality of divider sets are positioned in a different sequential portion of the passage to divide that passage portion into a predetermined number of sub passages, whereby the flow passage is sequentially divided into an increasing number of sub flow passages progressing from the inlet portion to the outlet portion. A larger device can be assembled using a parallel plurality of the basic devices.

19 Claims, 18 Drawing Sheets

(51) Int. Cl.
  *F15D 1/04* (2006.01)
  *F15D 1/00* (2006.01)
  *A61M 16/08* (2006.01)
  *A61M 16/06* (2006.01)

(52) U.S. Cl.
  CPC ....... *A61M15/0086* (2013.01); *A61M 16/0866* (2014.02); *F15D 1/001* (2013.01); *F15D 1/0005* (2013.01); *F15D 1/04* (2013.01); *A61M 16/06* (2013.01); *A61M 2206/11* (2013.01)

(56) References Cited

U.S. PATENT DOCUMENTS

| | | | |
|---|---|---|---|
| 3,502,103 A | | 3/1970 | Verschuur Eke |
| 3,725,186 A | | 4/1973 | Lynch |
| 3,838,598 A | * | 10/1974 | Tompkins ................ 73/861.52 |
| 3,965,931 A | | 6/1976 | Skobel |
| 4,284,496 A | | 8/1981 | Newton |
| 4,690,332 A | | 9/1987 | Hughes |
| 4,737,288 A | | 4/1988 | Melis et al. |
| 4,945,929 A | | 8/1990 | Egilmex |
| 4,972,830 A | | 11/1990 | Wong et al. |
| 5,178,138 A | | 1/1993 | Walstrom et al. |
| 5,392,768 A | | 2/1995 | Johansson et al. |
| 5,435,297 A | | 7/1995 | Klein |
| 5,461,932 A | | 10/1995 | Hall et al. |
| 5,477,849 A | | 12/1995 | Fry |
| 5,495,985 A | | 3/1996 | Nehm et al. |
| 5,894,995 A | | 4/1999 | Mazzei |
| 5,904,139 A | | 5/1999 | Hauser |
| 5,937,908 A | | 8/1999 | Inoshiri et al. |
| 6,065,472 A | | 5/2000 | Anderson et al. |
| 6,245,243 B1 | | 6/2001 | Meurer |
| 6,510,870 B1 | | 1/2003 | Valaszkai et al. |
| 6,606,992 B1 | | 8/2003 | Smith et al. |
| 6,626,169 B2 | | 9/2003 | Gaitini |
| 6,679,250 B2 | | 1/2004 | Walker et al. |
| 6,698,422 B2 | | 3/2004 | Fugelsang et al. |
| 6,810,874 B1 | | 11/2004 | Koskela et al. |
| 6,990,974 B2 | * | 1/2006 | Staniforth et al. ....... 128/200.18 |
| 7,089,963 B2 | * | 8/2006 | Meheen .......................... 138/44 |
| 7,781,548 B2 | | 8/2010 | Fitzgerald et al. |
| 2002/0026935 A1 | | 3/2002 | Schmidt et al. |
| 2004/0035412 A1 | | 2/2004 | Staniforth et al. |
| 2004/0216735 A1 | | 11/2004 | Fugelsang et al. |
| 2005/0172955 A1 | * | 8/2005 | Sundaram et al. ....... 128/200.23 |
| 2006/0169280 A1 | | 8/2006 | Yama et al. |

OTHER PUBLICATIONS

V.S. Ivanova, I.J. Bunin, and V.I. Nosenko, Fractal Material Science: A New Direction in Materials Science, Emerging technologies Overview, Jan. 1998, p. 52.

J P Mitchell, Spacers and holding chambers: Not the last word, we hope, Arch Dis Child 2001; 84:89 (January) p. 1-2.

H J Zar, M Maim, E G Weinberg, Spacers and holding chambers: Not the last word, we hope- a reply, Arch Dis Child 2001; 84:281 (March), p. 1-2.

Aerochamber Plus; Aerochamber Plus Valved Holding Chamber (VHC) device is the #1 prescribed holding chamber for use with inhaled asthma medications; Forest Laboratories, Inc.; www.frx.com/products/aerochamber.aspx. p. 1-2.

Directions for Use, AeroChamber Plus, 2001,2005 Forest Laboratories, Inc.; 1 page.

AeroChamber Plus has significant advantages compared to the original AeroChamber, AeroChamber Plus Valved Holding Chamber; Product Information; www.aerochambervhc.com/patient/. p. 1-2.

H J Zar, E G Weinberg, H J Binns, F Gallie, M D Mann, Lung deposition of aerosol-a comparison of different spacers, Arch Dis Child 2000; 82 495-498 (June), p. 1-9.

Harvey Marcovitch, Archives this month, Arch Dis Child 2000; 82: (June); p. 1-4.

* cited by examiner

FLOW MODIFICATION DEVICE

RELATED APPLICATION

This is a continuation-in-part of application Ser. No. 11/975,592, filed Oct. 19, 2007, entitled "Flow Modification Device", now U.S. Pat. No. 8,371,291, which application claimed the benefit of provisional Application Ser. No. 60/853,347, filed Oct. 19, 2006, and entitled "Flow Modification Device", both hereby incorporated by reference.

BACKGROUND OF THE INVENTION

1. Field

The invention is in the field of devices to improve the properties of fluid flowing in a passage, particularly fluids containing particles therein. The invention is also in the field of improving the flow properties of an aerosol fluid containing medications prior to inhalation of the fluid by a patient to improve the delivery of the medications through the patient air passages to the lungs.

2. State of the Art

There are many instances where it is desired to lessen turbulence in flowing fluids and create or maintain laminar flow of such fluids. For example, a large number of people suffer from respiratory diseases such as bronchitis, emphysema, and asthma. The symptoms of these diseases in many cases can be reduced by medications inhaled into the lungs by the patient. The medications are typically dispensed from a hand held aerosol dispenser into a housing through which the patient breaths to pull air with the medication droplets therein in through the mouth, down the throat, and into the lungs.

A problem with these treatments is that a major percentage of the medication is deposited in the mouth, throat, and trachea of the patient as the air travels from the mouth to the lungs. With some devices, a significant amount of the medication is also deposited in the device itself, before reaching the mouth. Thus, this medication does not reach the lungs where it is needed, but is wasted and can cause side effects as it contacts and is absorbed by the surfaces of the mouth, throat, and trachea, or as it is swallowed. In many instances, the medication dispenser is a metered dose inhaler set to deliver a specific dose of medication. However, with a major percentage of the medication not reaching the lungs, the dosing is of little value.

While this problem has been recognized in the prior art, most attempts to reduce the problem have focused on ensuring small, uniform medication droplet size (such as uniform droplets in the range of one to three microns) and better and more uniform suspension of the medication droplets in the air to be breathed into the lungs. In many cases this is done by directing the spray of medicine into a spacer or expansion chamber to allow better mixing of the medicine droplets with the air to be breathed prior to breathing of the air. The spacer or chamber also acts as a reservoir to hold the air with medicine therein until breathed by the user, thereby lessening the need for the user to coordinate spraying the medicine with the inhalation of the air containing the medicine.

Spacer devices are often hollow cylindrical, conical, or bottle shaped tubes. One end of the tube has a place where a medicine pump can be attached. The other end of the tube may or may not have a valve, and may or may not have a mask attached. Examples of various spacers or mixing chambers are shown in U.S. Pat. Nos. 4,690,332, 4,972,830, 5,435,297, 5,477,849, and 6,698,422, and the AEROCHAMBER PLUS® product is shown at www.aerochambervhc.com. While providing more uniform, small sized droplets monodispersed into the air to be breathed and providing a reservoir for the air has been found to result in more of the medication reaching the lungs, room for improvement remains.

SUMMARY

The inventor has theorized that at least part of the problem causing deposition of particles suspended in a fluid stream is turbulence in the fluid stream that directs the travel of the particles at angles to the direction of flow of the fluid stream, causing the particles to impact the walls of the flow passages constraining the stream. If turbulence can be reduced, i.e., if more laminar flow of the fluid can be induced, the particles will tend to flow with the stream and the impacting of the particles against the walls defining the flow passage will be reduced. In the particular application to inhalation of aerosol medication, while control of the flow of the air with medication droplets therein is lost once it is inhaled, if a laminar flow with both air and suspended droplets or particles traveling in substantially the same direction at substantially the same speed is provided as the air and medication droplets enter the patient's mouth, the droplets will tend to remain suspended in and travel with the air as it is drawn through the patient's mouth, throat, and trachea, and into the lungs, better than if the droplets are already traveling in various different directions when inhaled. This pre-alignment of air and droplet travel reduces the amount of medicine droplets that will leave the air stream and impact the mouth, throat, and trachea as the air flows to the lungs resulting in more of the medicine actually reaching the lungs.

According to the invention, an air passage, similar to a cylindrical spacer used with an aerosol medicine dispenser, is provided with a plurality of dividers therein to align and guide the flow of air and particles to be inhaled by the patient. This alignment and guidance is provided by sequentially and systematically dividing the initial single flow passage into a larger number of smaller flow passages. This provides a sequential and gradual systematic subdivision of the flow through the passage into multiple smaller flows according to certain rules of subdivision (algorithm). For example, a cylindrical spacer device may form a flow passage extending from an inlet end adapted to receive the outlet of a medication dispenser, such as a metered dose inhaler which produces an aerosol spray of medication droplets at the passage inlet end, and an outlet end to communicate with an air inlet of a patient, such as the patient's mouth. The flow passage may be divided into a plurality of sequential passage portions, with an initial passage portion of preset length forming a single passage adjacent the inlet end. At the end of this initial passage portion, a first intermediate passage portion of preset length may have a divider positioned therein to divide the single passage of the initial portion in half thereby dividing the single passage into two parallel smaller sub flow passages. At the end of the first intermediate portion, a second intermediate portion of preset length may have a divider positioned therein to divide each of the two smaller sub flow passages of the first intermediate portion in half to form four separate parallel smaller sub flow passages. At the end of the second intermediate passage portion, an outlet end passage portion adjacent the outlet end of the passage and of preset length may have a divider positioned therein to divide each of the four sub flow passages of the second intermediate passage portion in half to provide eight parallel smaller sub flow passages. This continued dividing of the passages into smaller passages can continue as desired and as dictated by the overall length of the passage to maintain a laminar flow through the passages which will maintain most of the particles in the fluid and reduce the number of particles impacting the walls of the passage. With the embodiment of the invention directed to use as a spacer for medication inhalation, the first passage portion which is a single passage into which the aerosol medication is sprayed, may be longer than other passage portions and will be dimensioned so as to serve the same purposes of the prior art spacers in providing a reservoir of substantially small medicine droplets suspended in the air to be breathed. The remaining portions of the passage with the dividers therein then act to align and guide the flow of air with medicine droplets therein as the air is breathed in through the passage by the patient to provide a substantially laminar flow of air and droplets into the mouth of the patient.

Further, the device of the invention may be modularized in that the basic device described as providing a fluid passage with a plurality of dividers therein to sequentially and gradually systematically divide the initial single flow passage into a larger number of smaller flow passages as flow through the device progresses, may be used as small modules clustered together in parallel to provide a combined output having the increased laminar flow and particle suspension desired. With such clustered multiple devices, various sizes of devices of the invention can easily be formed to simultaneously provide a multiple of the number of increased smaller flow passages provided by any one basic device in the same length device. For example, as described above, a basic device of the invention may sequentially and gradually systematically divide in four steps an initial single flow passage into two, and then four, and then eight smaller sub flow passages in a preset length. If two of these basic devices are clustered in parallel and connected in a single flow passage, the two devices initially divide the single flow passage into two smaller sub flow passages, one into each of the two parallel devices, which then divide each of the two sub flow passages into two, four, and eight smaller sub flow passages to provide sixteen smaller sub flow passages in the same preset length as the single device would provide eight smaller sub flow passages. Similarly, if ten of these basic devices are clustered in parallel and connected to a single flow passage, the ten devices initially divide the single flow passage into ten smaller sub flow passages, one into each of the ten parallel devices, which then each divide each of the ten sub flow passages into the two, four, and eight smaller sub flow passages to provide eighty smaller sub flow passages in the same preset length as the single device would provide eight smaller sub flow passages. Further, where different basic devices are clustered in parallel, a wide variety of desired results can flexibly be achieved.

THE DRAWINGS

In the accompanying drawings, which show the best mode currently contemplated for carrying out the invention:

DETAILED DESCRIPTION OF THE ILLUSTRATED EMBODIMENTS

Figure 1:
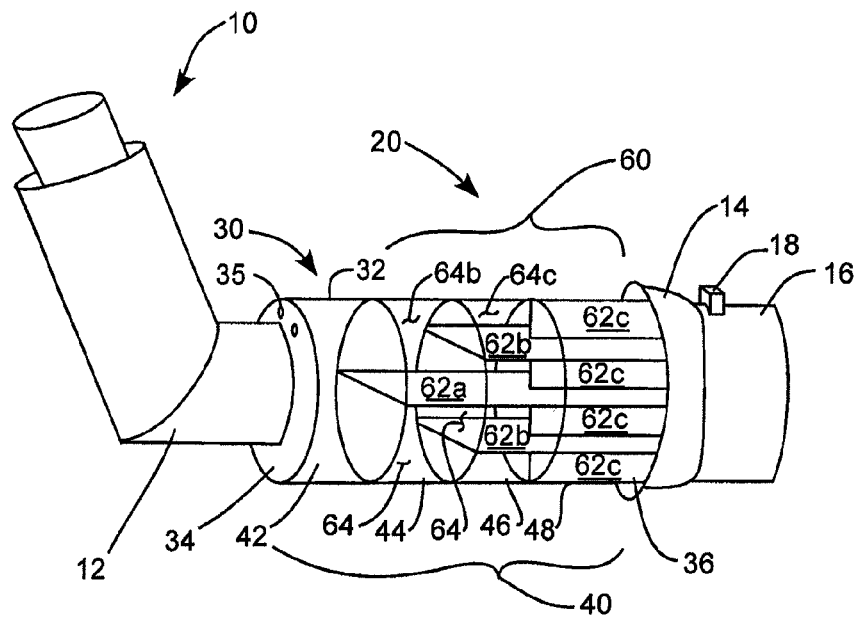
FIG. 1 is a perspective view of an air flow device in accordance with an embodiment of the present invention shown coupled to an aerosolized medication inhaler.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The embodiments of the present invention described herein are generally directed to an air passage similar to a cylindrical spacer used with an aerosol medicine dispenser. The air passage is provided with a plurality of divider sets with each divider set positioned sequentially along a length of the air passage. The divider sets align and guide the flow of air and particles to be inhaled by the patient and divide the initial single flow passage into a larger number of smaller flow passages. The divider sets provide a sequential and gradual systematic subdivision of the flow through the passage into multiple smaller flows according to certain rules of subdivision. The rules of subdivision can follow a predetermined geometric progression defined by a mathematical algorithm.

For example, a cylindrical spacer device may form a flow passage extending from an inlet end adapted to receive the outlet of a medication dispenser, such as a metered dose inhaler which produces an aerosol spray of medication droplets at the passage inlet end, and an outlet end to communicate with an air inlet of a patient, such as the patient's mouth. The flow passage may be divided into a plurality of sequential passage portions, with an initial passage portion of preset length forming a single passage adjacent the inlet end. At the end of this initial passage portion, a first intermediate passage portion of preset length may have a divider positioned therein to divide the single passage of the initial portion in half thereby dividing the single passage into two parallel smaller sub flow passages. At the end of the first intermediate portion, a second intermediate portion of preset length may have a divider positioned therein to divide each of the two smaller sub flow passages of the first intermediate portion in half to form four separate parallel smaller sub flow passages. At the end of the second intermediate passage portion, an outlet end passage portion adjacent the outlet end of the passage and of preset length may have a divider positioned therein to divide each of the four sub flow passages of the second intermediate passage portion in half to provide eight parallel smaller sub flow passages. This continued dividing of the passages into smaller passages can continue as desired and as dictated by the overall length of the passage to maintain a laminar flow through the sub flow passages which will maintain the suspension of most of the particles in the fluid and reduce the number of particles impacting the walls of the passage.

With the embodiment of the invention directed to use as a spacer for medication inhalation, the first passage portion, which is a single passage into which the aerosol medication is sprayed, may be longer than other passage portions and will be dimensioned so as to serve the same purposes of the prior art spacers in providing a reservoir of substantially small medicine droplets suspended in the air to be breathed. The remaining portions of the passage with the dividers therein then act to align and guide the flow of air with medicine droplets therein as the air is breathed in through the passage by the patient to provide a substantially laminar flow of air and droplets into the mouth of the patient.

Figure 2:
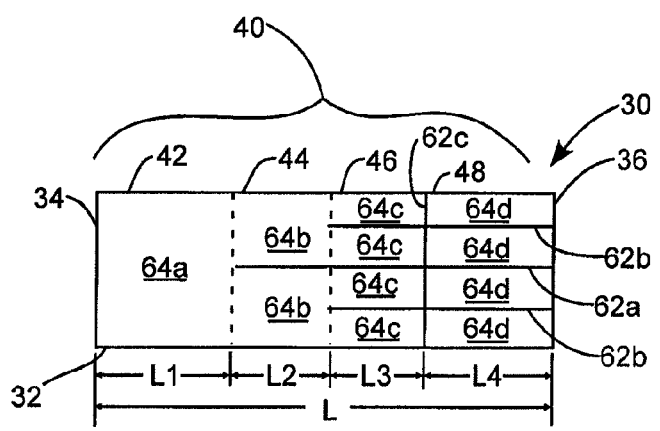
FIG. 2 is a cross-sectional side view of a flow passage of the air flow device of FIG. 1.
Figure 3:
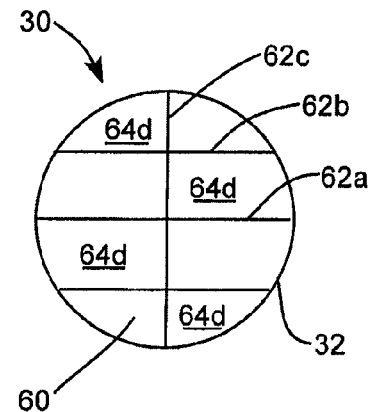
FIG. 3 is a cross-sectional end view of a flow passage of the air flow device of FIG. 1.

Accordingly, as illustrated in FIGS. 1-3, an air flow device, indicated generally at 20, is shown in accordance with an embodiment of the present invention for providing and maintaining laminar flow of a fluid and maintaining particle suspension in the fluid during fluid flow. The air flow device includes a flow passage, indicated generally at 30, and a plurality of divider sets, indicated generally at 60, sequentially positioned within the flow passage.

In one aspect, the flow passage 30 is formed by a tube 32 having a substantially cylindrical shape. The tube 32 has a longitudinal length, designated as L, that is bounded by two ends, an inlet end 34 and an outlet end 36. The inlet end 34 and outlet end 36 are opposite ends of the tube 32 and air flow moves in the direction from the inlet end toward the outlet end. The tube 32 can be formed of a polymeric material such as plastic and may be transparent, translucent, or opaque.

Figure 4:
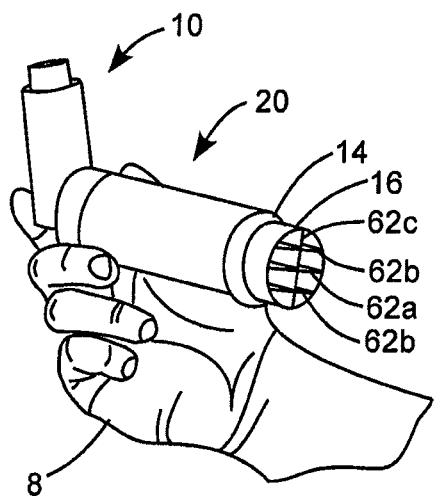
FIG. 4 is a perspective view of the air flow device of FIG. 1 shown being held in the hand of a patient.
Figure 5:
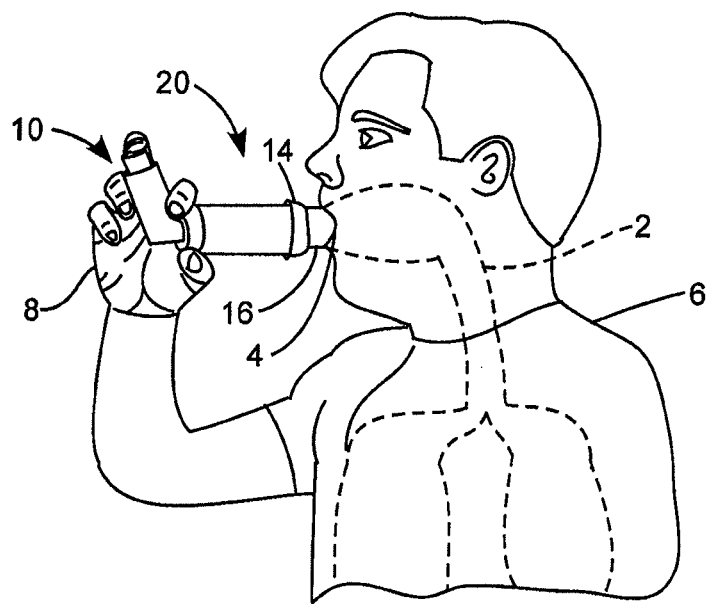
FIG. 5 is a perspective view of the air flow device of FIG. 1 shown directing flow of medicine into the airway of a patient.

In one embodiment, the air flow device 20 is directed to use as a spacer for medication inhalation, such as a pressurized metered dose inhaler, as is commonly used to treat asthma or other respiratory ailments. In this embodiment, the flow passage 30 acts as a spacer structure, similar to inhaler spacers as known in the art. The inlet end 34 is adapted to receive the outlet 12 of a medication dispenser, indicated generally at 10, such as an asthma inhaler that can be held in a patient's hand 8, as shown in FIG. 4. The outlet end 36 has an adapter 14 to communicate with an air inlet of a patient 6, such as the patient's mouth 4. In this embodiment, fluid, such as air mixed with medicine, flows through the flow passage 30 of the spacer from the inlet end 34 toward the outlet end 36 and into the patient's airway when the patient breathes in. Thus, the patient sucks the medicine from the spacer into the patient's airway, as shown in FIG. 5. Generally, the connection between the outlet 12 of the medication dispenser 10 and the inlet end 34 of the air flow device 20 is not air tight so that air can flow into the inlet end 34 of the air flow device 20 as the patient sucks the air and medicine through the air flow device. If necessary for relatively free air flow, holes 35 can be provided in the inlet end 34.

Referring again to FIGS. 1-3, a mouthpiece 16 is coupled to the air flow device 20 at the outlet end 36. The mouthpiece is sized and shaped to fit into a patient's mouth 4 and to facilitate delivery of fluid from the air passage 30 to the patient's airway 2. Also, while the mouthpiece 16 is sized and shaped to fit into a patient's mouth 4, it is also sized and shaped, along with adapter 14, to maintain as much as possible the laminar flow created by the air flow device 20 as the air and medication flows from the outlet end 36 of the air flow device 20, through the adapter 14 and mouthpiece 16, and into the patient's mouth 4.

Additionally, a valve 18 can be coupled to the air flow device 20 to restrict fluid movement through the flow passage 30 until desired by the user. The valve 18 can be configured to allow flow of fluid through the flow passage only in a direction from inlet end to outlet end. It will be appreciated that pressurized metered dose inhalers disperse aerosolized medicine into the air which is then inhaled by the patient. It is often desirable for the aerosolized medicine to have time to thoroughly mix with the surrounding air prior to being inhaled so as to ensure a substantially uniform dispersal of medicine throughout the inhaled air in order to maximize the effectiveness of the medicine. Advantageously, the valve 18 keeps the air and medicine in the flow passage 30 until the valve is opened. In this way, the medicine can be allowed to thoroughly mix with the air prior to being inhaled by the patient.

The flow passage 30 is divided into a plurality of sequential portions, indicated generally at 40, between the inlet end 34 and the outlet end 36. In one embodiment, the sequential portions 40 include an inlet portion 42 extending into the flow passage 30 from the inlet end 34 and an outlet portion 48 disposed at the opposite end of the flow passage from the inlet portion 42. Additionally, the flow passage 30 includes at least one intermediate passage portion between the inlet portion 42 and the outlet portion 48. In one aspect, the flow passage 30 can include a first intermediate portion 44 and a second intermediate portion 46.

The plurality of divider sets 60 are positioned inside the tube 32 with each divider set positioned in a different sequential portion of the flow passage 30 so as to divide that portion of the flow passage into a predetermined number of additional sub flow passages 64a, 64b, 64c, and 64d. The plurality of divider sets 60 includes partitions 62a, 62b, and 62c that divide the flow passage 30 into the smaller sub flow passages 64a, 64b, 64c, and 64d. The partitions 62a, 62b, and 62c cross the inside of the tube 32 and extend longitudinally along the tube to the outlet end 36 of the flow passage 30. The partitions 62*a*, 62*b*, and 62*c* can be formed of a polymeric material such as plastic and can be transparent, translucent, or opaque.

In one aspect, the partitions 62*a*, 62*b*, and 62*c* can be oriented at angles with respect to one another such that the partitions intersect one another to form the sub flow passages 64*a*, 64*b*, 64*c*, and 64*d*. In the embodiment shown in FIG. 1, the partitions 62*a*, 62*b*, and 62*c* are oriented parallel and orthogonal to one another to form sub flow passages 64*a*, 64*b*, 64*c*, and 64*d* with straight sides formed by the partitions 62*a*, 62*b*, and 62*c* and arcuate or curved sides formed by the cylindrical wall of the tube 32.

Additionally, the divider sets 60 are arranged such that at least one of the subsequent sub flow passages 64*c* is smaller than at least one of the preceding passages 64*b* in the preceding divider set. In this way, the divider sets 60 split the flow passage 30 sequentially into a larger number of sub flow passages 64*a*, 64*b*, 64*c*, and 64*d* progressing from the inlet end 34 of the flow passage to the outlet end 36 of the flow passage.

Thus, the plurality of the sets of dividers 60 partition the flow passage 30 into an increasing number of sub flow passages 64*a*, 64*b*, 64*c*, and 64*d* according to the position of the sequential portion of the flow passage 30 with respect to the outlet end 36. Specifically, the portions of the flow passage 30 closer to the inlet end 34 have fewer sub flow passages 64*a*, 64*b*, 64*c*, and 64*d* and the portions of the flow passage closer to the outlet end 36 have more sub flow passages.

Accordingly, the inlet portion 42 of the flow passage 30 has a preset length, L1, and no dividers so that the inlet portion is a single passage 64*a* adjacent the inlet end 34. It will be appreciated that the length L1 of the inlet portion 42 of the passage 30 may be relatively longer than lengths of the subsequent portions 44, 46, and 48 of the flow passage so as to facilitate mixing of the medicine from the inhaler 10 with the air in the flow passage 30 prior to subdividing the passage in subsequent portions of the flow passage.

At the end of the inlet portion 42, a first intermediate passage portion 44 of preset length, L2, has a single divider 62*a* positioned therein which divides the single passage 64*a* of the initial portion 42 in half to form two parallel smaller sub flow passages 64*b* that extend through the first intermediate portion 44. At the end of the first intermediate portion 44, a second intermediate portion 46 of preset length, L3, has another divider 62*b* positioned therein which divides each of the two smaller sub flow passages 64*b* of the first intermediate portion 44 in half to form four separate parallel smaller sub flow passages 64*c* that extend through the second intermediate portion 46. At the end of the second intermediate portion 46, an outlet end portion 48 adjacent the outlet end 36 of the passage 30 and of preset length, L4, has another divider 62*c* positioned therein to divide each of the four sub flow passages 64*c* of the second intermediate portion 46 in half to provide eight parallel smaller sub flow passages 64*d* that extend through the outlet portion 48. In this way, the fluid in the flow passage 30 is aligned and guided from the inlet end 34 of the flow passage to the outlet end 36 of the flow passage.

Additionally, it will be appreciated that the length of each portion of the flow passage 30 can be shorter the closer the portion is to the outlet end 36. Thus, the sub flow passages of each subsequent portion can have both a smaller volume and a shorter length than the sub flow passages of the preceding portion. However, the lengths of each passage portion can vary in different ways, such as the inlet portion and outlet portion being longer than the intermediate portions as shown in FIGS. 1 and 2, or all portions may be of equal length.

It should be noted that, as shown in FIGS. 1-3, once a sub flow passage is formed, it does not reconnect with any other sub flow passage until all sub flow passages end at the outlet of the flow passage 30 where all sub flow passages combine into whatever chamber or passage the flow passage 30 discharges into, such as adapter 14 and mouthpiece 16, or directly into a user's mouth. Each sub flow passage in one flow passage portion is directly divided into additional smaller sub flow passages in the next sub flow portion. In the above described embodiment shown in FIGS. 1-3, each sub flow passage in one flow passage portion is directly divided in half into two smaller sub flow passages upon entering the next sub flow portion. This direct division of one sub flow passage into two smaller connected sub flow passages maintains the integrity of all sub flow passages and of the fluid flowing in the passages, i.e., all fluid flowing in one sub flow passage is divided and flows directly into the connected divided sub flow passages and once in a sub flow passage, there is no mixing of fluid flowing in one sub flow passage with fluid flowing in another sub flow passage. Only fluid in the sub flow passage that is divided flows into the connected divided sub flow passages. In this way, the flow passage is sequentially divided into an increasing number of sub flow passages in each flow passage portion progressing from the inlet end of the passage to the outlet end of the passage.

The subdivision of the flow passage 30 can be determined according to a pre-selected algorithm. In one aspect, the algorithm can conform to a mathematical rule, such as a geometric progression. The algorithm may also take into account the length of the flow, the cross sectional area, and the volume of the flow passage or sub flow passages. For example, the algorithm may predetermine that each new divider subdivides the existing flow passage into two new sub flow passages, as illustrated in FIG. 1. In this case, the ratio of cross sectional areas of the two newly formed sub flow passages in each subsequent portion of the flow passage will be approximately 2:1, and the sum of the cross sectional areas of each individual sub flow passage approximately equals the cross sectional area of the original flow passage. Additionally, the length of the newly formed sub flow passages in each subsequent portion of the flow passage 30 can be approximately $9/10^{th}$ of the preceding sub flow passage. Thus, the algorithm can be used to predetermine a fixed ratio of cross sectional areas and a fixed ratio of lengths for each sub flow passage.

It will be appreciated that other algorithms for subdividing the flow passage 30 can also be used. For example, the concepts of the present invention contemplate algorithms for dividing the flow passage that take into account physical properties of the fluid and/or substance being suspended or mixed with the fluid traveling through the flow path. As another example, a random placement of dividers throughout the flow passage may be desirable and can be used with the flow passage described herein. As yet another example, the algorithm may also predetermine the shape of the flow passage and/or the shape of the dividers in the flow passage. Thus, the algorithm for determining subdivision of the flow passage can be tailored to meet the intended usage of the flow device 10.

It will also be appreciated that the number of passage portions needed to maintain laminar flow, and if particles are suspended in the fluid, to maintain the particles in suspension, will vary with the distance the fluid needs to travel and the particular fluid and, if present, the particular characteristics of the particles. Many shapes of passages and many configurations of dividers to divide the passages into more passages can be used. Usually, the configuration of dividers and lengths of passage portions will be determined by particular formulas or algorithms that have been determined as applicable for the particular situation where the invention is used.

It will be further appreciated that if necessary to help maintain the established laminar flow from the outlet end portion 48 of the device, the dividers from the outlet portion 48 can extend into the adapter 14 and mouthpiece 16 interfacing the outlet end 36 of the device with the patient's mouth 4, as shown in FIG. 4.

Figure 6:
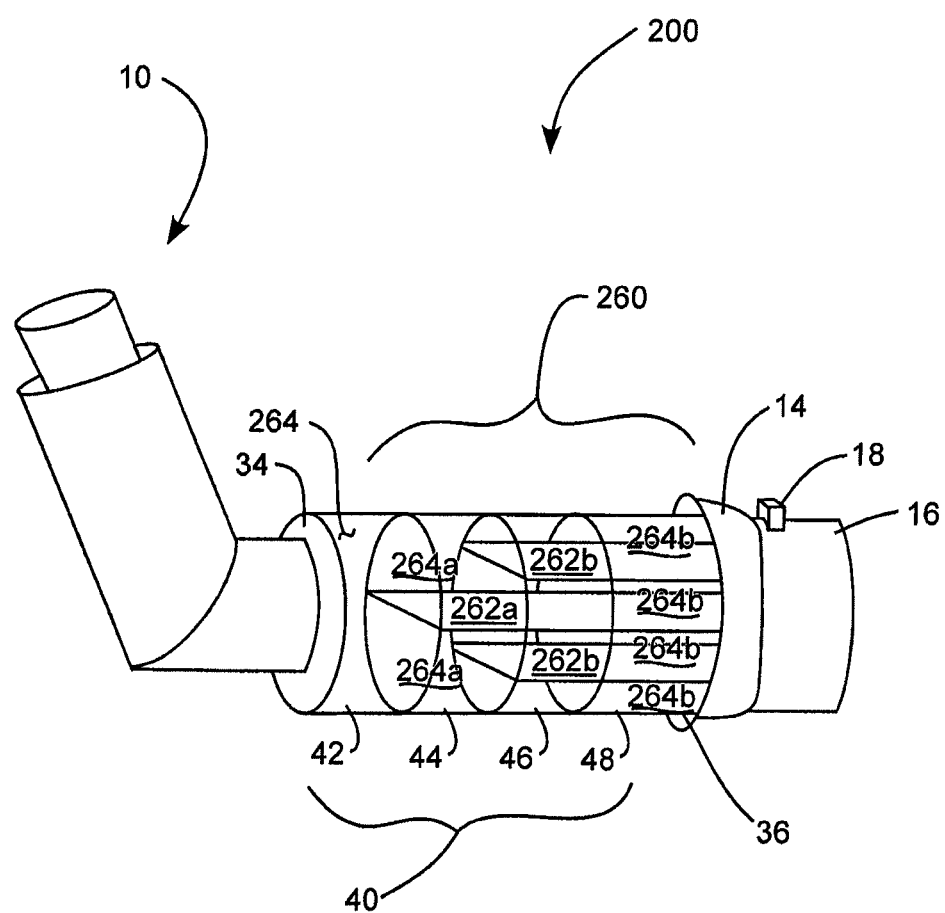
FIG. 6 is a perspective view of an air flow device in accordance with another embodiment of the present invention.

Accordingly, as illustrated in FIG. 6, an air flow device, indicated generally at 200, is shown in accordance with another embodiment of the present invention for providing and maintaining laminar flow of a fluid and maintaining particle suspension in the fluid during fluid flow. The air flow device 200 is similar in many respects to the air flow device 20 described above and shown in FIGS. 1-3. The air flow device includes a flow passage, indicated generally at 30 and a plurality of divider sets, indicated generally at 260, sequentially positioned within the flow passage.

The flow passage 30 has a plurality of sequential portions, indicated generally at 40, including an inlet portion 42 adjacent an inlet end 34, a first intermediate portion 44, a second intermediate portion 46, and an outlet portion 48 adjacent an outlet end 36. The dividers 260 disposed in the flow passage 30 include partitions 262a and 262b that divide the flow passage 30 into sub flow passages 264, 264a and 264b. The partitions 262a and 262b include a central partition 262a positioned in the flow passage 30 after the inlet portion 34 to divide the flow passage into two substantially equal sub flow passages 264a in the first intermediate portion 44. Additional partitions 262b are positioned in the flow passage 30 after the first intermediate portion 44 to divide each of the sub flow passages 264a in the first intermediate portion into two substantially equal sub flow passages 264b, thereby forming four sub-flow passages 364b in the second intermediate portion 46 and the outlet portion 48. In this embodiment, the portion of the passage with the four sub-flow passages 364b is longer than the portions with the one and two sub-flow passages.

Figure 7:
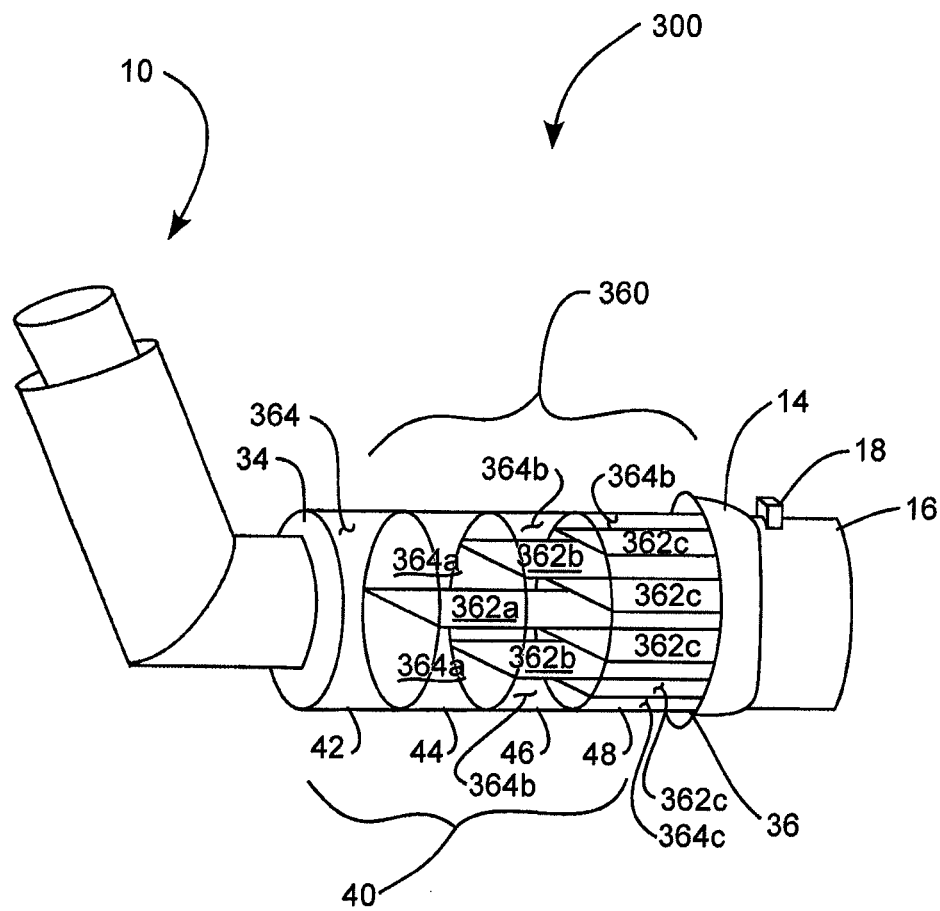
FIG. 7 is a perspective view of an air flow device in accordance with another embodiment of the present invention.

As illustrated in FIG. 7, an air flow device, indicated generally at 300, is shown in accordance with another embodiment of the present invention for providing and maintaining laminar flow of a fluid and maintaining particle suspension in the fluid during fluid flow. The air flow device 300 is similar in many respects to the air flow devices 20 and 200 described above and shown in FIGS. 1-3 and FIG. 6, respectively. The air flow device 300 includes a flow passage, indicated generally at 30 and a plurality of divider sets, indicated generally at 360, sequentially positioned within the flow passage.

The flow passage 30 has a plurality of sequential portions, indicated generally at 40, including an inlet portion 42 adjacent an inlet end 34, a first intermediate portion 44, a second intermediate portion 46, and an outlet portion 48 adjacent an outlet end 36. The divider sets 360 disposed in the flow passage 30 include partitions 362 that divide the flow passage 30 into sub flow passages 364. The partitions 362 include a central partition 362a positioned in the flow passage 30 after the inlet portion 34 to divide the flow passage into two substantially equal sub flow passages 364a in the first intermediate portion 44. Additional partitions 362b are positioned in the flow passage 30 after the first intermediate portion 44 to divide each of the sub flow passages 364a in the first intermediate portion into two substantially equal sub flow passages 364b, thereby forming four sub-flow passages 364b in the second intermediate portion 46. Similarly, additional partitions 362c are positioned in the flow passage 30 after the second intermediate portion 46 to divide each of the sub flow passages 364b in the second intermediate portion 46 into two substantially equal sub flow passages 364c, thereby forming eight sub-flow passages 364c in the outlet portion 48.

Figure 8:
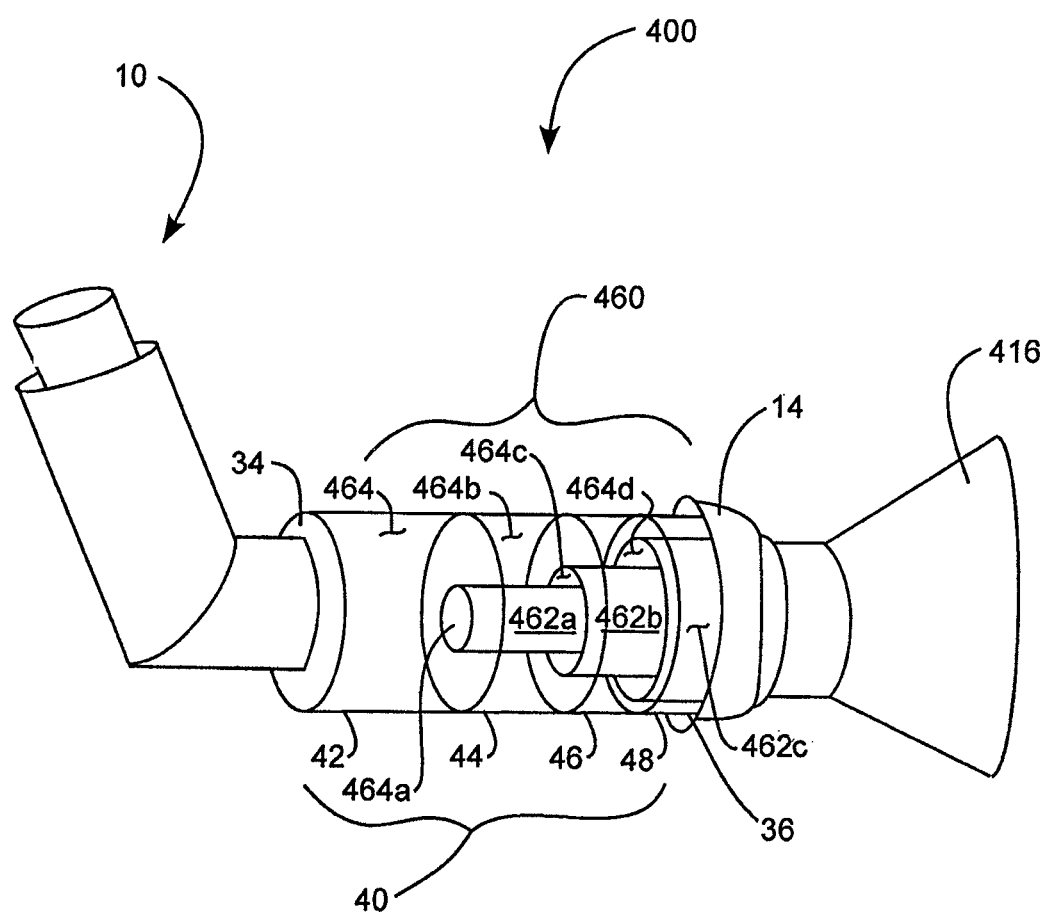
FIG. 8 is a perspective view of an air flow device in accordance with another embodiment of the present invention.

As illustrated in FIG. 8, an air flow device, indicated generally at 400, is shown in accordance with another embodiment of the present invention for providing and maintaining laminar flow of a fluid and maintaining particle suspension in the fluid during fluid flow. The air flow device 400 is similar in many respects to the air flow devices 20, 200, and 300 described above and shown in FIGS. 1-3, FIG. 6, and FIG. 7, respectively. The air flow device 400 includes a flow passage, indicated generally at 30 and a plurality of divider sets, indicated generally at 460, sequentially positioned within the flow passage.

The flow passage 30 has a plurality of sequential portions, indicated generally at 40, including an inlet portion 42 adjacent an inlet end 34, a first intermediate portion 44, a second intermediate portion 46, and an outlet portion 48 adjacent an outlet end 36. The dividers 460 disposed in the flow passage 30 include partitions 462a, 462b, and 462c that divide the flow passage 30 into sub flow passages 464a, 464b, 464c, and 464d. The partitions 462a, 462b, and 462c are cylindrically shaped and divide the flow passage 30 into circular or annular sub flow passages. Specifically, the partitions 462a, 462b, and 462c include a central partition 462a positioned in the flow passage 30 after the inlet portion 42 to divide the flow passage into an inner sub flow passage 464a and an outer sub flow passage 464b in the first intermediate portion 44. An additional partition 462b is positioned in the flow passage 30 after the first intermediate portion 44 to divide the outer sub flow passage 464b in the first intermediate portion 44 into a first intermediate sub flow passage 464c and an outer sub flow passage 464b thereby forming three sub-flow passages in the second intermediate portion 46. Similarly, an additional partition 462c is positioned in the flow passage 30 after the second intermediate portion 46 to divide the outer sub flow passage 464b in the second intermediate portion 46 into a second intermediate sub flow passage 464d and an outer sub flow passage 464b thereby forming four sub-flow passages in the outlet portion 48.

Additionally, a face mask 416 is coupled to the outlet end 48 to facilitate delivery of fluid from the air flow device to the patient's airway. The face mask 416 can be configured to fit over the mouth or the mouth and nose of the patient.

Figure 9:
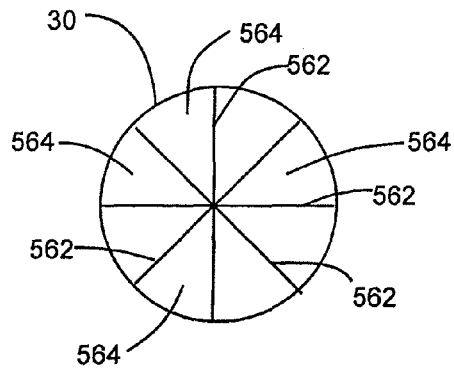
FIGS. 9-14 are cross sectional views of a flow passage of an air flow device such as shown in FIG. 1 showing different configurations of partitions dividing the flow passage into sub flow passages.
Figure 10:
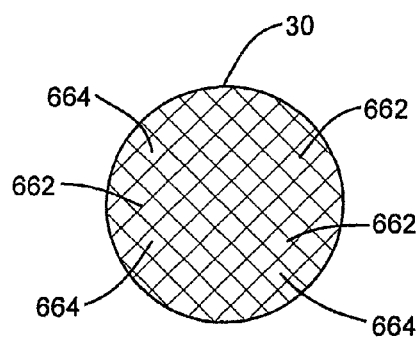
Figure 11:
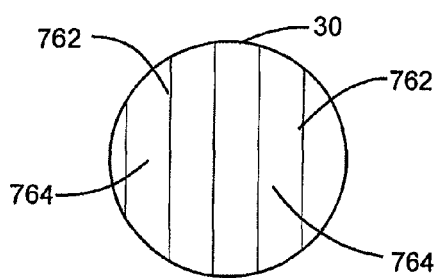
Figure 12:
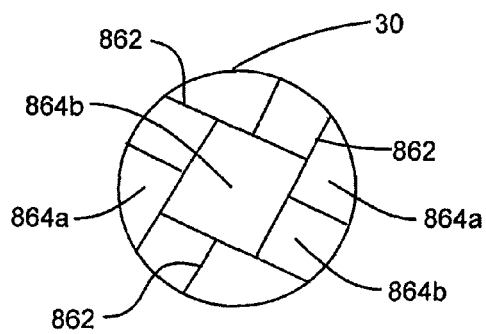
Figure 13:
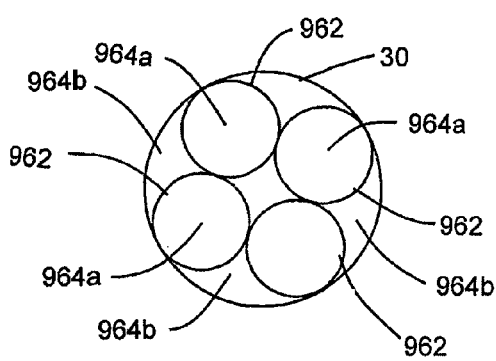
Figure 14:
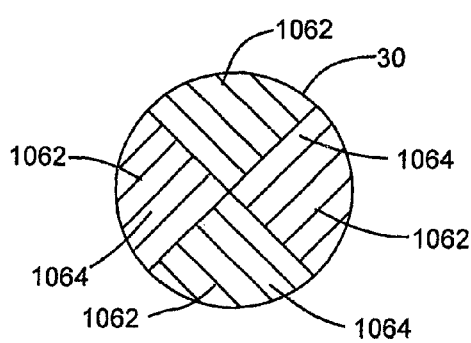

As illustrated in FIGS. 9-14, other divider arrangements are shown for use in an air flow device 20 described above and shown in FIGS. 1-3. FIG. 9 illustrates a cross section of a flow passage 30 with radial partitions 562 dividing the flow passage into wedge shaped sub flow passages 564. FIG. 10 illustrates a cross section of a flow passage 30 with crisscross partitions 662 dividing the flow passage into diamond shaped sub flow passages 664. FIG. 11 illustrates a cross section of a flow passage 30 with substantially vertical and parallel partitions 762 dividing the flow passage into vertical sub flow passages 764. FIG. 12 illustrates a cross section of a flow passage 30 with partitions 862 dividing the flow passage into a patchwork pattern with substantially triangular sub flow passages 864a and quadrangular sub flow passages 864b. FIG. 13 illustrates a cross section of a flow passage 30 with partitions 962 dividing the flow passage into circular sub flow passages 964a and arcuate sub flow passages 964b. FIG. 14 illustrates a cross section of a flow passage 30 with partitions 1062 dividing the flow passage into a mixture of orthogonally oriented segmented sub flow passages 1064.

It will be appreciated that the partitions can divide the flow passage 30 into any number of patterns to facilitate parallel flow, axial flow, radial flow, concentric flow, alternating flow, and the like. Additionally, the partitions can be symmetrically or asymmetrically placed within the flow passage.

While the embodiments of FIGS. 1-8 have all shown the inlet single flow passage divided into two smaller sub flow passages, such as by being divided in half, with the two smaller sub flow passages then each divided into two smaller sub flow passages, such as by again being divided in half, the inlet single flow passage can be initially divided into any number of smaller sub flow passages, and each of the smaller sub flow passages can also be divided into any number of still smaller sub flow passages. Further, it has been found that a plurality of the tubular devices described so far, particularly if of a relatively small size (small diameter), can be clustered together in parallel to form smaller sub flow passages of a larger flow passage device of the invention. Thus, if ten of the tubular devices of the invention are clustered together in parallel in a larger single flow passage, the single flow passages in the inlet portion of each of the ten parallel tubular devices will divide the larger single flow passage in which the ten devices are clustered into ten sub flow passages. Each of these ten sub flow passages are then divided into additional sub flow passages in the manner described above.

Figure 15A:
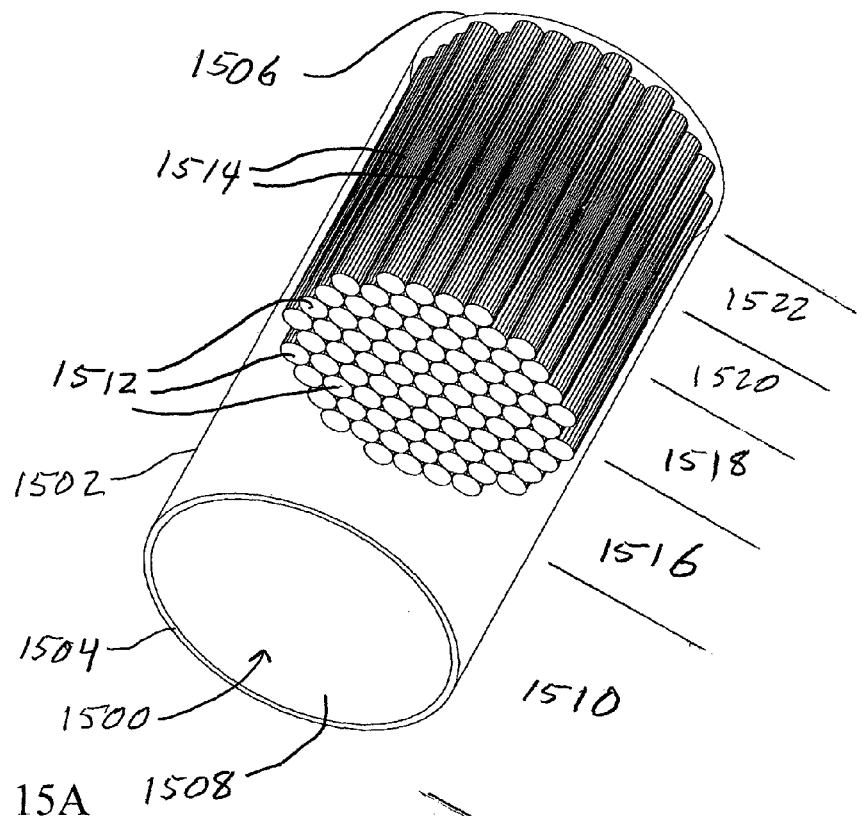
FIG. 15A is a perspective view of an air flow device in accordance with an embodiment of the invention using a plurality of basic air flow devices of the invention clustered in parallel.
Figure 15B:
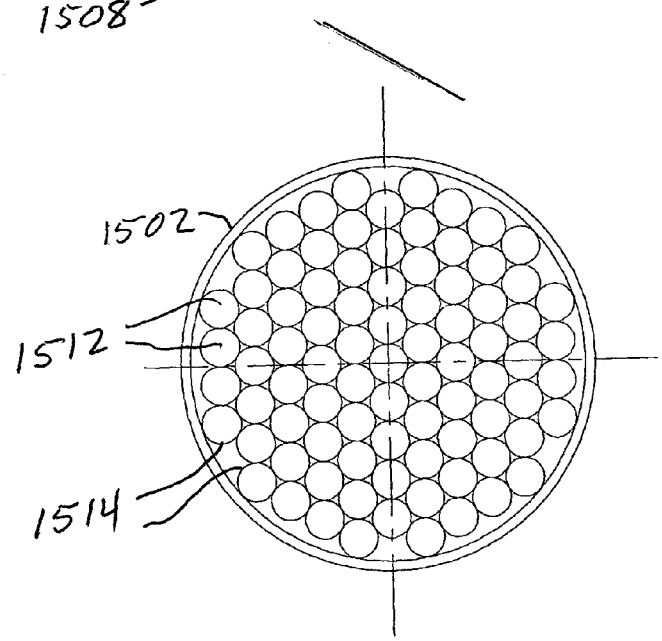
FIG. 15B is an inlet end view of the air flow device of FIG. 15A.

FIGS. 15A and 15B show a flow passage 1500 formed by a tube 1502 having an inlet end 1504 and an outlet end 1506 and being of substantially cylindrical shape, which flow passage and tube can correspond to the flow passage 30 formed by cylindrical tube 32 as shown in FIGS. 1-5. As such, the device of FIGS. 15A and 15B can be sized to serve as a spacer for a medication inhaler as shown in FIGS. 1-5. However, the single inlet flow passage 1508 forming the flow passage inlet portion 1510 of tube 1502 is divided initially into a plurality of smaller sub flow passages 1512, here shown as eighty-five smaller sub flow passages 1512, with each sub flow passage 1512 formed by a smaller tube 1514. The tubes 1514 are arranged together side-by-side within tube 1502 with all the inlet ends of all smaller tubes 1514 aligned and all outlet ends of all smaller tubes 1514 aligned and aligned with the outlet end 1506 of the larger tube 1502. The single inlet passage 1508 forms the inlet flow passage portion 1510 of the device corresponding to the inlet flow passage portion 42 of the device of FIGS. 1-5. The aligned inlet ends of the smaller tubes 1514 forming the sub flow passages 1512, forms the end of the inlet flow passage potion 1510 and the beginning of the first intermediate portion 1516 of the passage 1500, corresponding to first intermediate portion 44 of FIGS. 1-5. Thus, the single inlet flow passage 1508 is divided into a plurality of smaller sub flow passages 1512, each of the passages 1512 formed by each of the smaller tubes 1514, forming a sub flow passage.

Each smaller tube 1514 can comprise a tubular device of the invention, such, for example, as shown in FIGS. 1-5. Thus, each smaller tube 1514 can be a smaller diameter version of the device shown in FIG. 1-5 having dividers therein to further divide each sub flow passage 1512 into additional smaller sub flow passages along the length of the tube 1514. For example, each tube 1514 can be constructed with divider sets therein, not shown, similar to the divider sets shown in FIGS. 1-5, wherein each of the sub flow passages 1512 would be divided in half into two further smaller sub flow passages in a first intermediate passage portion (passage portion 44 of FIGS. 1-5) of each smaller tube 1514, which would form a second intermediate portion 1518 of the device of FIG. 15A, would be divided again in half into two further smaller sub flow passages in a second intermediate passage portion (passage portion 46 of FIGS. 1-5) of each smaller tube 1514, which would form a third intermediate portion 1520 of the device of FIG. 15A, and would be divided again in half into two further smaller sub flow passages in an outlet passage portion (passage portion 48 of FIGS. 1-5) of each smaller tube 1514, which would form an outlet portion 1522 of the device of FIG. 15A resulting in each of the sub flow passages 1512 being divided into eight smaller sub flow passages by the outlet end of each smaller tube 1514, which is also the outlet end of tube 1502. While the tubes 1514 can be constructed similarly to the tubes 30 of FIGS. 1-5, such tubes 1514 are of much smaller diameter so that the plurality of such tubes used can fit side-by-side into a tube of about the same diameter of tube 30 of FIGS. 1-5. Rather than the same pattern and number of sequential divisions as shown in FIGS. 1-5, various other division patterns and numbers of sequential divisions can be provided in each of the tubes 1514. Thus, the smaller tubes 1514 form the intermediate and outlet sequential portions of the device formed by larger tube 1502. Since the tubes 1514 are much smaller, i.e., of much smaller diameter, than the tube 1502, depending upon the size of tubes 1514, which may depend upon how many smaller tubes 1514 are clustered together in larger tube 1502, small tubes 1514 may be configured to provide only one division of the sub flow passage 1512 wherein tubes 1514 would provide one intermediate passage portion and the output passage portion for the device of FIGS. 1-5.

FIGS. 15A and 15B show a simple example of the concept of using a plurality of tubular devices of the invention to provide the sub flow passages of a larger device of the invention. FIGS. 15A and 15B show the plurality of the smaller tubular devices of the invention all of cylindrical shape having substantially the same length arranged in side-by-side configuration inside, and substantially filling, a larger tube of cylindrical shape. However, various arrangements and shapes of the smaller tubes within the larger tube can be used.

Figure 16:
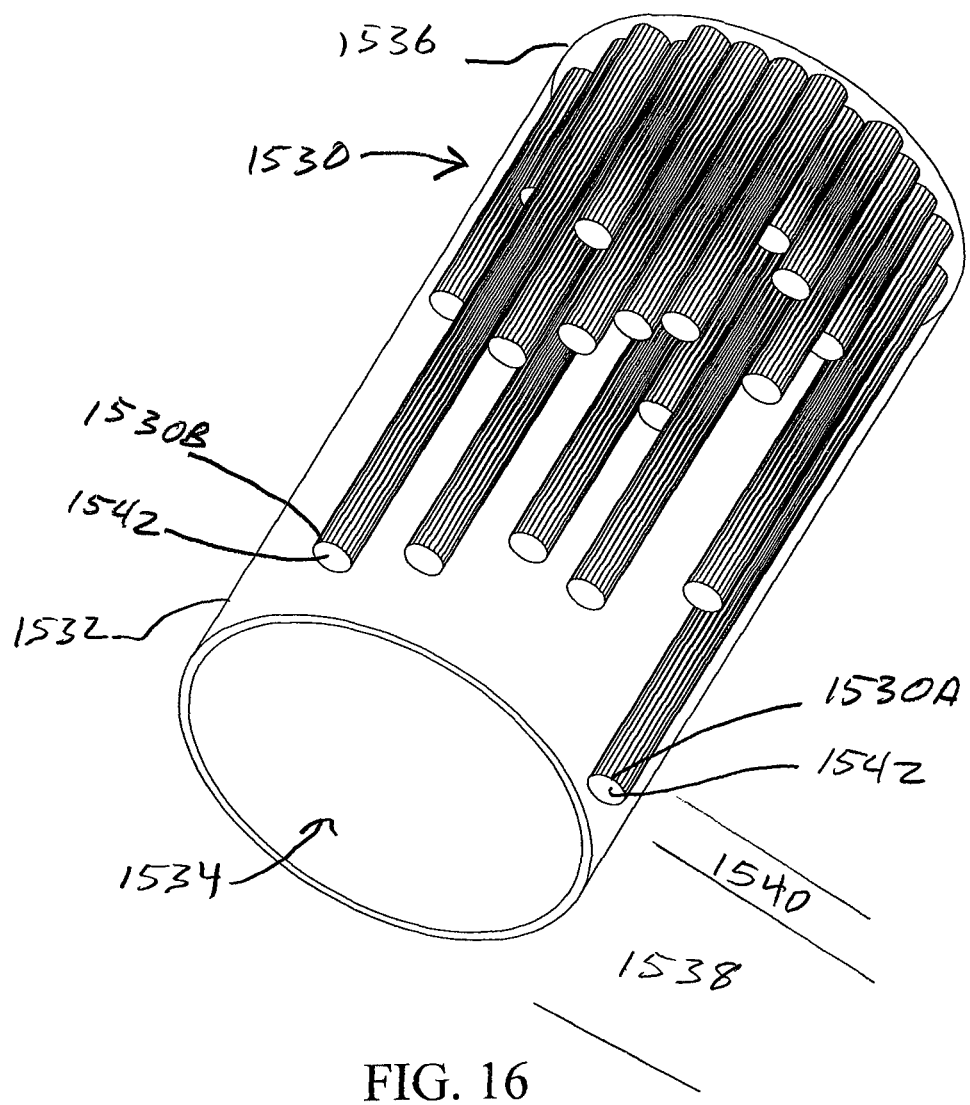
FIG. 16 is a perspective view similar to that of FIG. 15A showing a parallel cluster of different basic air flow devices.

FIG. 16 shows a plurality of smaller tubes 1530 of different lengths arranged side-by-side to substantially fill a larger tube 1532 forming a passage 1534 therethrough. All of the smaller tubes 1530 have outlet ends aligned at the outlet end 1536 of the larger tube 1532. FIG. 16 shows each smaller tube 1530 of a different length. This, in effect, divides the passage 1534 through larger tube 1532 into a large number of intermediate portions as the inlet end of each smaller tube 1530 starts a new sub flow passage which divides the flow passage at the respective smaller tube inlet into at least two sub flow passages and begins a new intermediate zone. For example, the single passage inlet portion 1538 of larger tube 1532 ends and the first intermediate portion 1540 begins with the inlet 1530A of the longest smaller tube 1530 which divides the single passage 1534 into sub flow passage 1542 through longest tube 1530 and the slightly smaller remaining area of passage 1534. The first intermediate portion 1540 ends and the second intermediate portion 1544 begins with the inlet 1530B of the next longest smaller tube 1530 which divides the slightly smaller remaining flow passage into a sub flow passage 1542 through the next longest tube 1530 and the slightly smaller remaining area of passage 1534. This division continues for each of the different length smaller tubes 1530. These different length smaller tubes provide the sequential division of the larger passage 1534 into smaller sub passages along the length of the larger tube.

While the different length smaller tubes provide the sequential division of the larger passage 1534 into smaller sub flow passages along the length of the larger tube, at least the longer of the tubes 1530 can also include internal divisions to divide the sub flow passages through such smaller tubes into additional sub flow passages, as previously described. The differences in lengths of the smaller tubes can also result in the larger tube 1532 being divided into sub flow passages of different size in each of the intermediate and outlet sequential portions of the passage 1534 along the length of larger tube 1532. This results from the continued subdivision of the sub flow passages in the longer tubes which provide smaller sub flow passages at the location where the shorter smaller tubes form sub flow passages which have not yet been further divided. Thus, the arrangement of FIG. 16 can provide a wide variety divisions and sub flow passages.

Figure 17A:
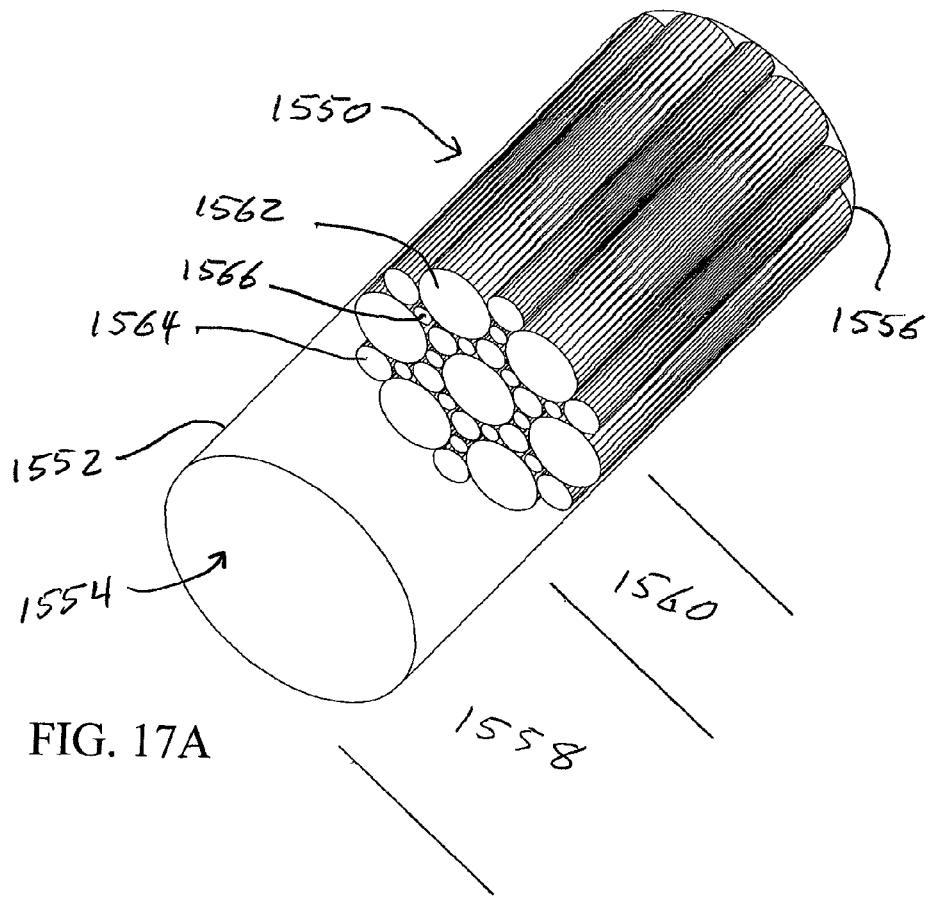
FIG. 17A is a perspective view similar to that of FIG. 15A showing a parallel cluster of still different basic air flow devices.
Figure 17B:
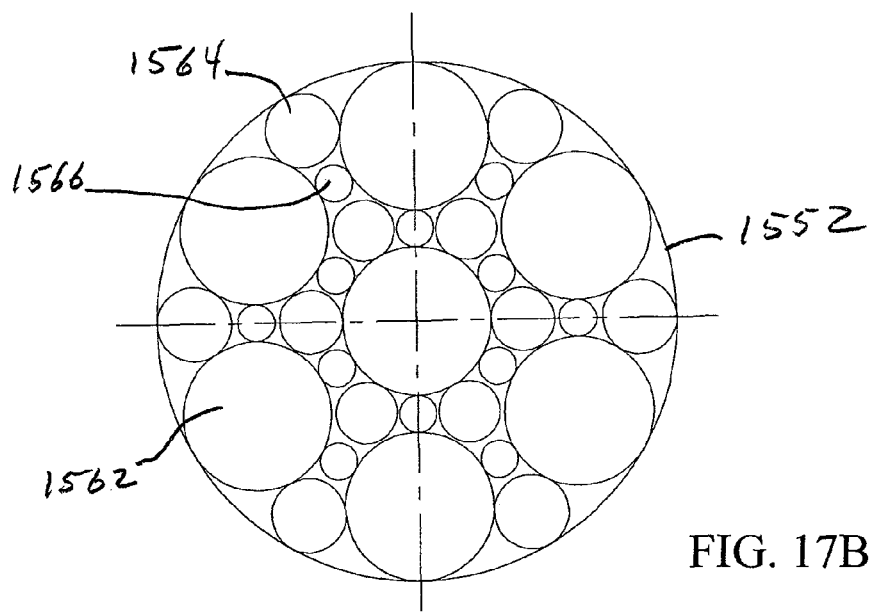
FIG. 17B is an inlet end view of the air flow device of FIG. 17A.

FIGS. 17A and 17B show a plurality of smaller tubes 1550 of different sizes (diameters) arranged side-by-side to substantially fill a larger tube 1552 forming a passage 1554 therethrough. All of the smaller tubes 1550 have outlet ends aligned at the outlet end 1556 of the larger tube 1552. Further, all of the smaller tubes 1550 have inlet ends aligned. Thus, the single inlet passage portion 1558 ends and the first intermediate passage portion 1560 begins with the aligned inlets of the various sized smaller tubes 1550. At this position along the large tube 1552, the single flow passage 1554 extending through the device inlet passage portion is divided into a plurality of sub flow passages 1562 of largest sub flow passage diameter, 1564 of medium sub flow passage diameter, and 1566 of smallest sub flow passage diameter. Again, the smaller tubes 1550 can be constructed with divider sets therein, not shown, wherein each of the sub flow passages 1562, 1564, and 1566 are divided into further sub flow passages along the length of the smaller tubes 1550. The end of the first intermediate flow passage portion 1560 is determined by where along any of the smaller tubes 1550 the first internal division of the first sub flow passage to be further divided takes place. The locations and numbers of the further intermediate flow passage portions depends upon the number and locations of the internal sub flow passage divisions.

Figure 18A:
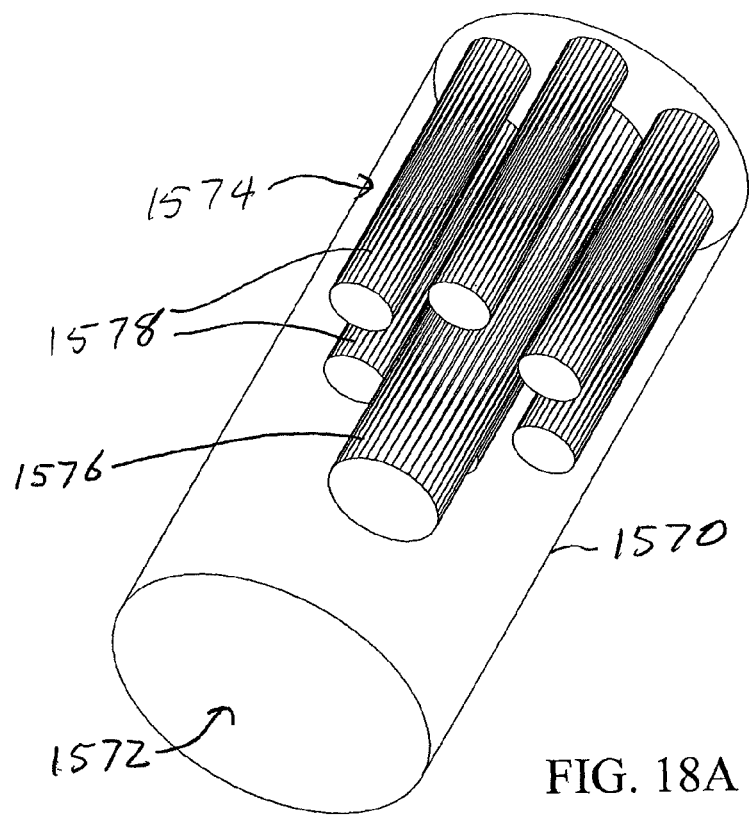
FIG. 18A is a perspective view similar to that of FIG. 15A showing a different parallel cluster of different basic air flow devices.
Figure 18B:
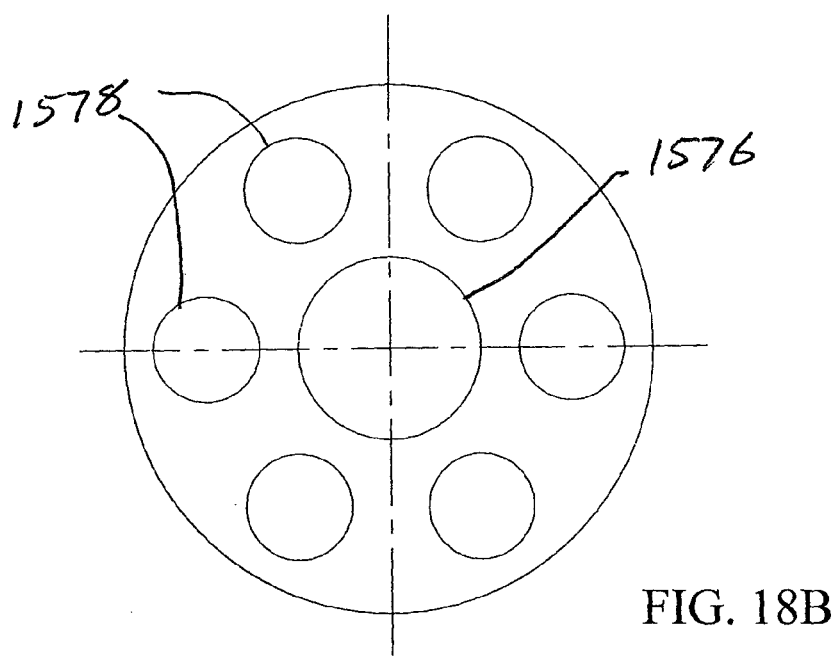
FIG. 18B is an inlet end view of the air flow device of FIG. 18A.

FIGS. 18A and 18B show an embodiment of the invention where a larger tube 1570 forming flow passage 1572 includes a plurality of smaller tubes 1574 arranged in parallel, spaced apart configuration. The tubes can be of various lengths and sizes, with FIG. 18 showing a single smaller central tube 1576 surrounded by six smaller tubes 1578. The spaced smaller tubes 1574 can be supported in larger tube 1570 in any suitable manner such as by supports, not shown, such as in the nature of a spider, extending between the inside wall of the larger tube 1570 to the respective smaller tubes 1574, or by a support at the outlet end of the various tubes. Such a support can be open to allow partial flow through passage 1572 without subdivision and partial flow with subdivision through sub flow passages through tubes 1574, or closed to force all flow through passage 1572 to be sub divided by flow through the spaced smaller tubes 1574.

Figure 19:
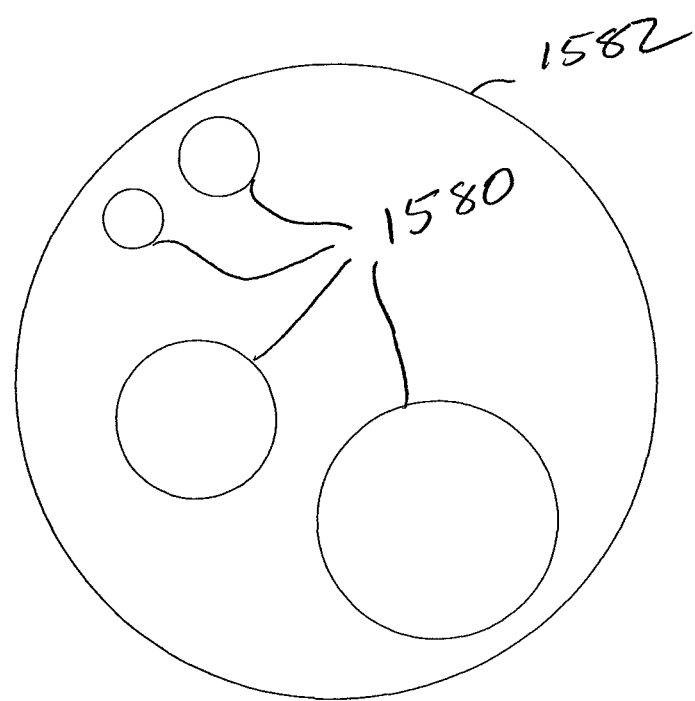
FIG. 19 is an inlet end view of a further embodiment of a parallel cluster of basic air flow devices.

While FIG. 18 shows the spaced smaller tubes 1574 arranged in a symmetrical pattern, the smaller tubes can be arranged in an asymmetrical pattern as shown in FIG. 19. FIG. 19 shows smaller tubes 1580 arranged in an asymmetrical pattern within larger tube 1582.

Figure 20A:
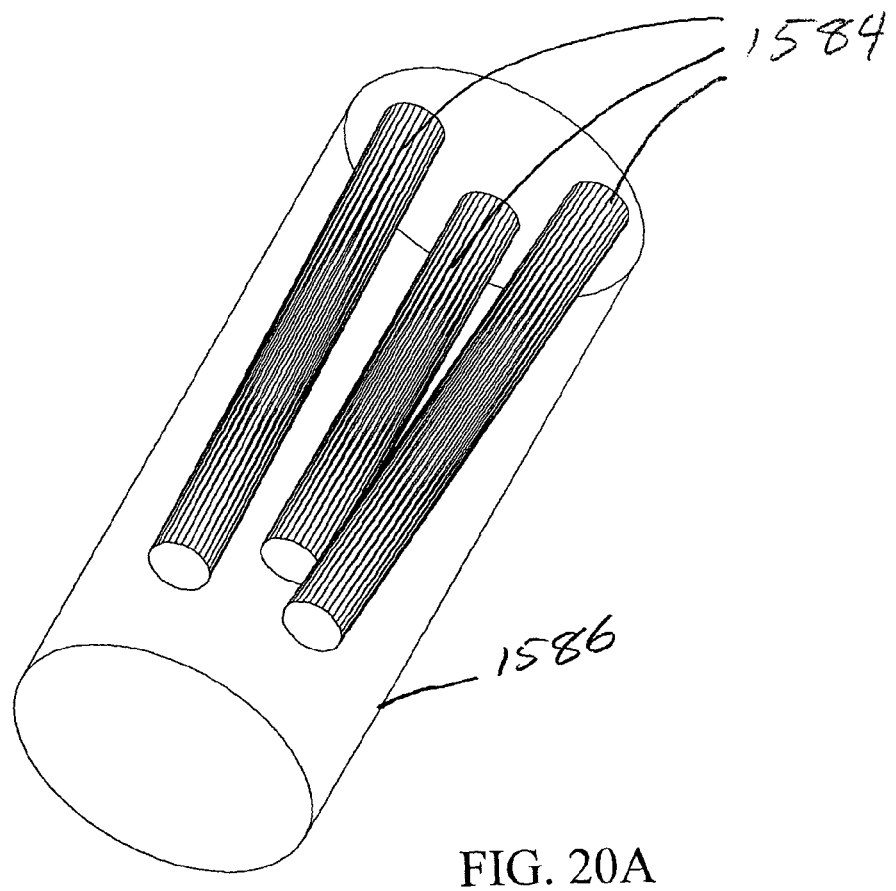
FIG. 20A is a perspective view similar to that of FIG. 15A showing a different arrangement of parallel cluster of basic air flow devices.
Figure 20B:
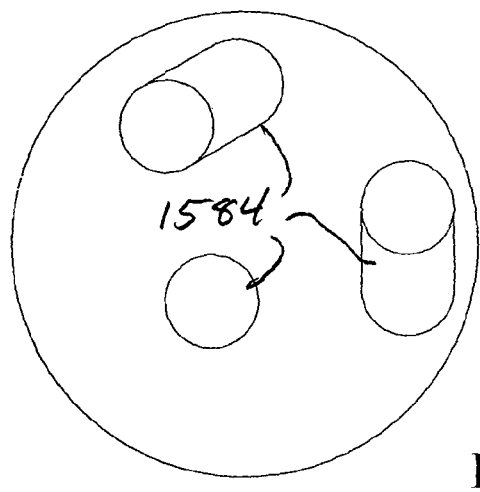
FIG. 20B is an inlet end view of the air flow device of FIG. 20A.

FIGS. 20A and 20B show three smaller tubes 1584 in non parallel spaced apart arrangement in larger tube 1586.

Figure 21:
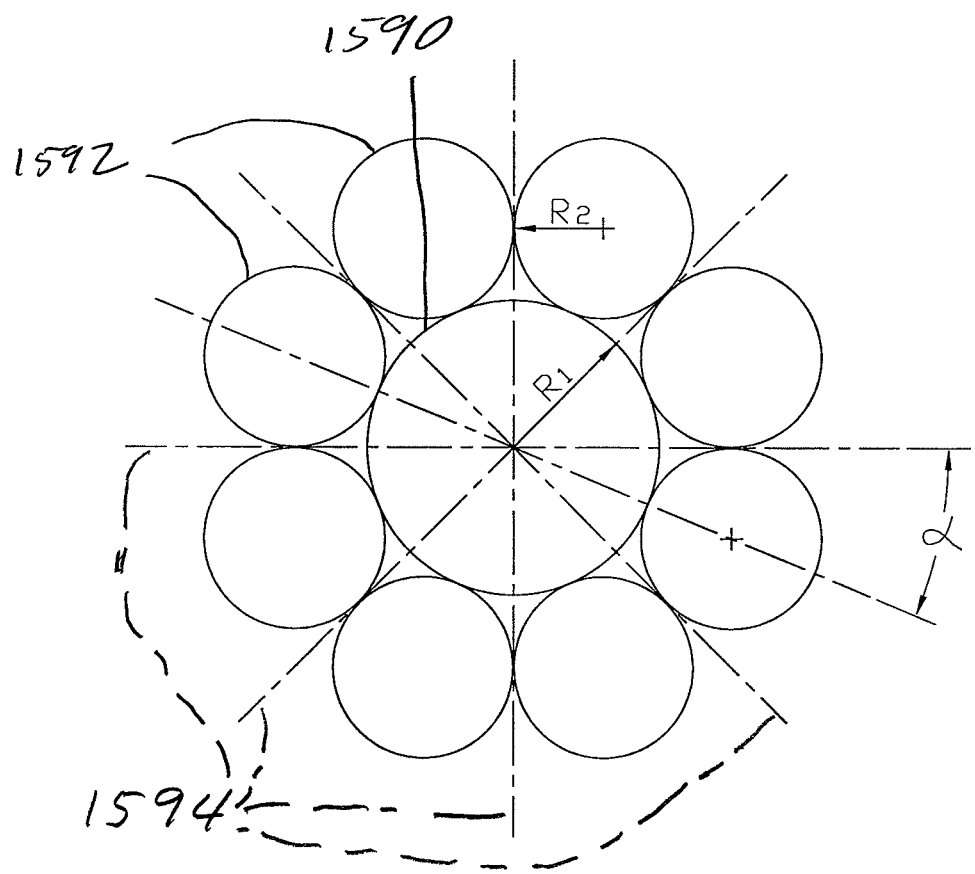
FIG. 21 is an inlet end view of an arrangement of a parallel cluster of basic air flow devices.

FIG. 21 shows a device of the invention, usable as a spacer, in which the individual tubes are of unequal lengths and diameters, and are clustered together in coextending fashion as compactly as possible. The central inner tube 1590 is cylindrical with a radius of R1, length of L1, and a cross sectional area of S1. The surrounding second layer consists of eight tubes 1592 with parameters of R2, L2, V2, and S2.

The volumes can be calculated as:

$$V1=S1*L1, V2=S2*L2.$$

Cross sectional areas can be calculated as:

$$S1=pi*R1^2, \text{ and } S2=pi*R2^2 < \alpha=360/16=22.5 \text{ deg}.$$

Figure 22:
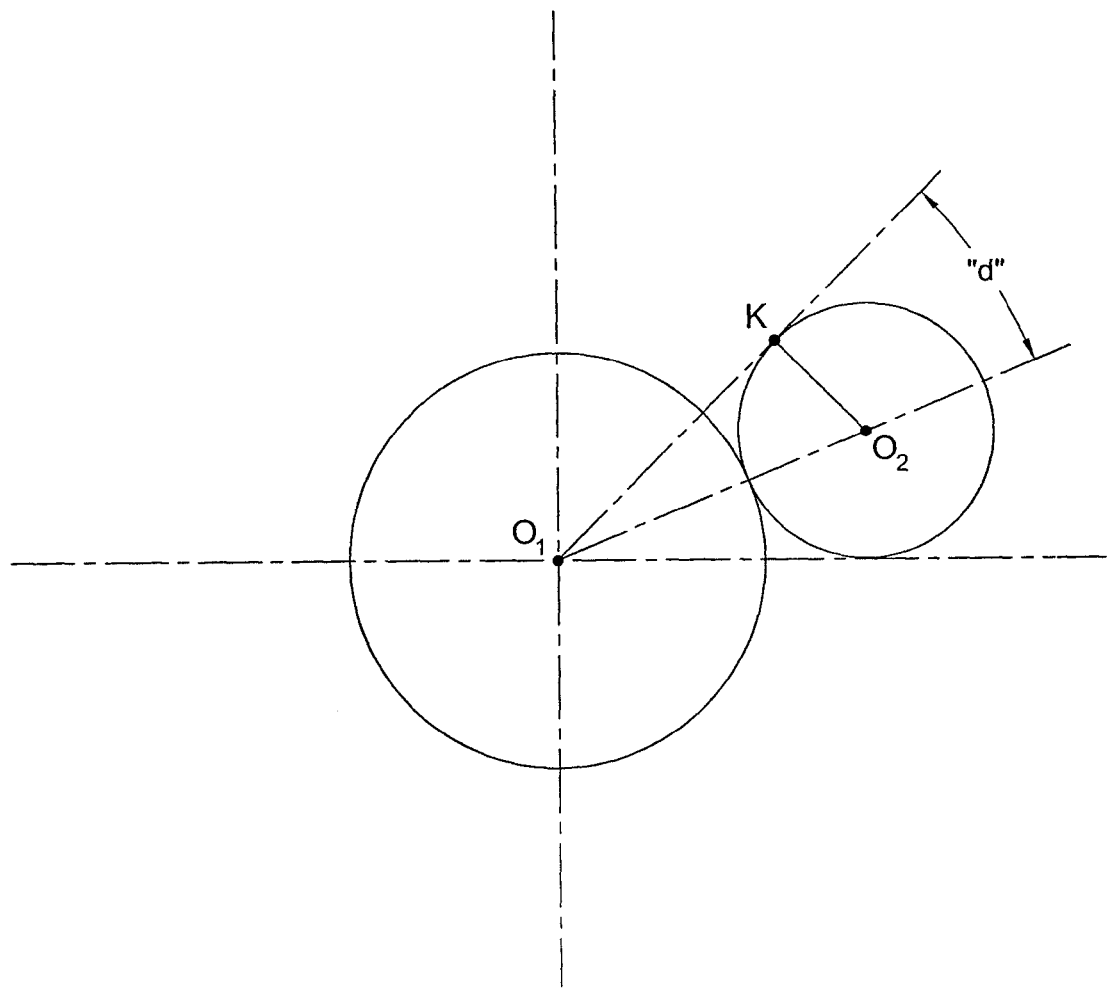
FIG. 22 shows a portion of the arrangement of FIG. 21.

Referring to FIG. 22

$$O_1O_2=R1+R2, KO_2=R2, \text{ and } <O_1KO_2=90 \text{ deg}.$$

Therefore:

$$R2/R1+R2=\sin \alpha \rightarrow R2=R1*\sin \alpha+R2*\sin \alpha \rightarrow R2*$$
$$(1=\sin \alpha)=R1*\sin \alpha \rightarrow R2/R1=\sin \alpha/(1-\sin \alpha)=0.62$$

The number of tubes in the second layer may be any number n>2 (in this particular case n=8).

The larger the number n is, the smaller the ratio R2/R1. When n=6, $<\alpha=30$ deg$\rightarrow \sin \alpha=\frac{1}{2}\rightarrow$R2/R1=1$\rightarrow$R2=R1

If for some reason all tubes are to be of equal volumes (there might be aerodynamic advantages to that similar to the ones demonstrated in some bronchial tree models), then we have $$V1=V2 \rightarrow S1*L1=S2*L2 \rightarrow pi*R1^2*L1=pi*R2^2*L2 \rightarrow$$
$$(R2/R1)^2=L1/L2$$

For n=6, L1/L2=1, and for n=8, L1/L2=0.38
For n>6, R2<R1, L2>L1, and for n<6, R2>R1, L2<L1
In practicality, the case of n>6, when the second layer of tubes is suppose to be longer than the central tube (L2>L1), becomes impossible to construct because the inner walls of the second layer of tubes create an extension to the central tube, making it really at least as long as the second layer tubes. Therefore, for V1=V2, n can only be equal to 3,4,5, or 6

Figure 23A:
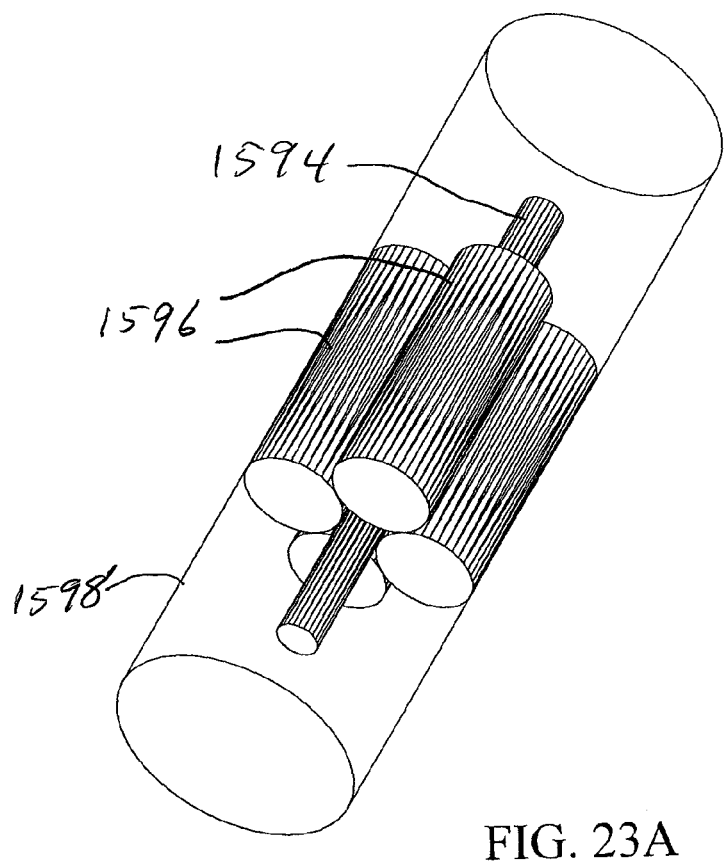
FIG. 23A is a perspective view similar to that of FIG. 15A showing a different arrangement of parallel cluster of basic air flow devices.
Figure 23B:
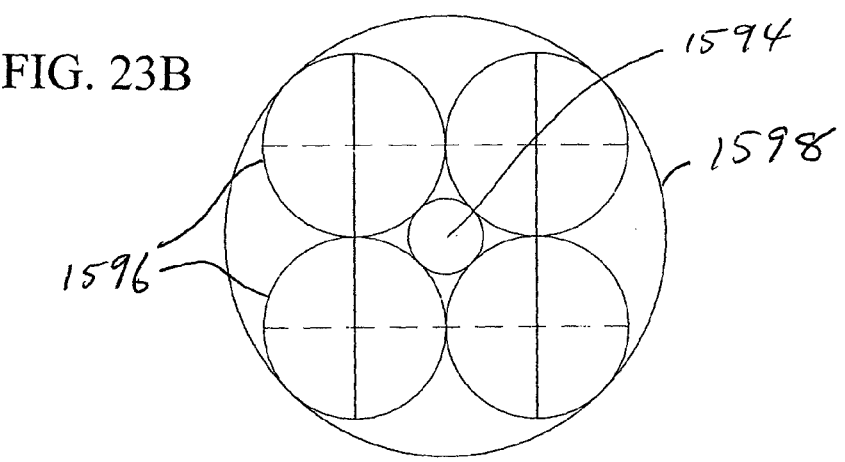
FIG. 23B is an inlet end view of the air flow device of FIG. 23A.

All ratios of parameters are predetermined, and are easily calculable. An example of a possible spacer device using the above calculations when n=4 is shown in FIGS. 23A and 23B. As shown, a smaller central tube 1594 is surrounded by four larger, but shorter, tubes 1596, which are all clustered inside of larger tube 1598.

Figure 24A:
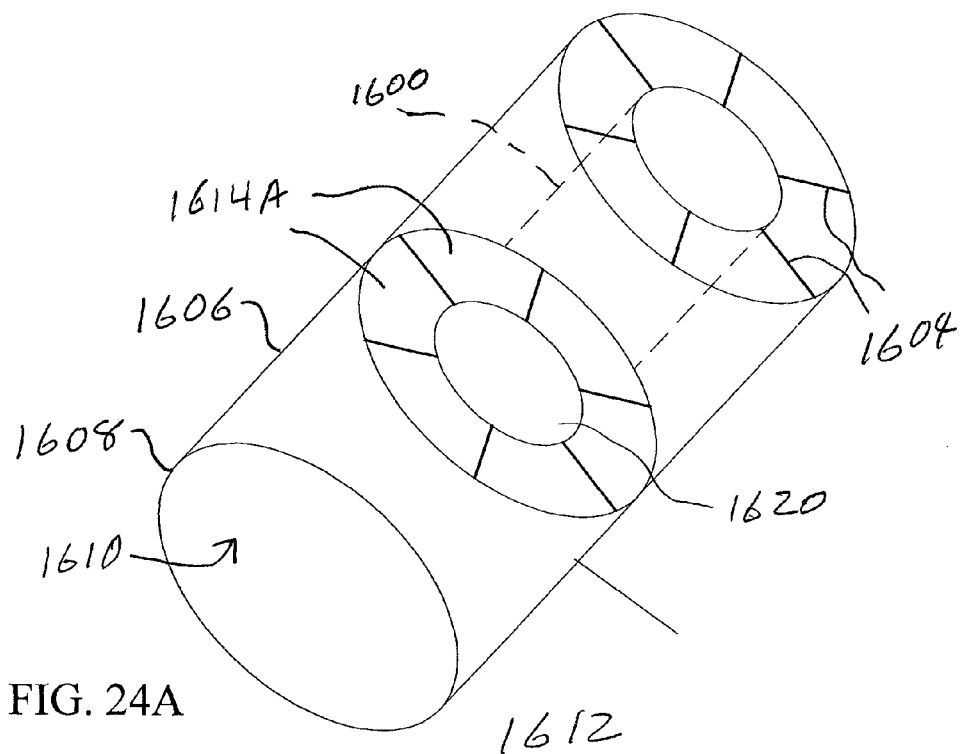
FIG. 24A is a schematic perspective view of a different arrangement of a parallel cluster of basic air flow devices.
Figure 24B:
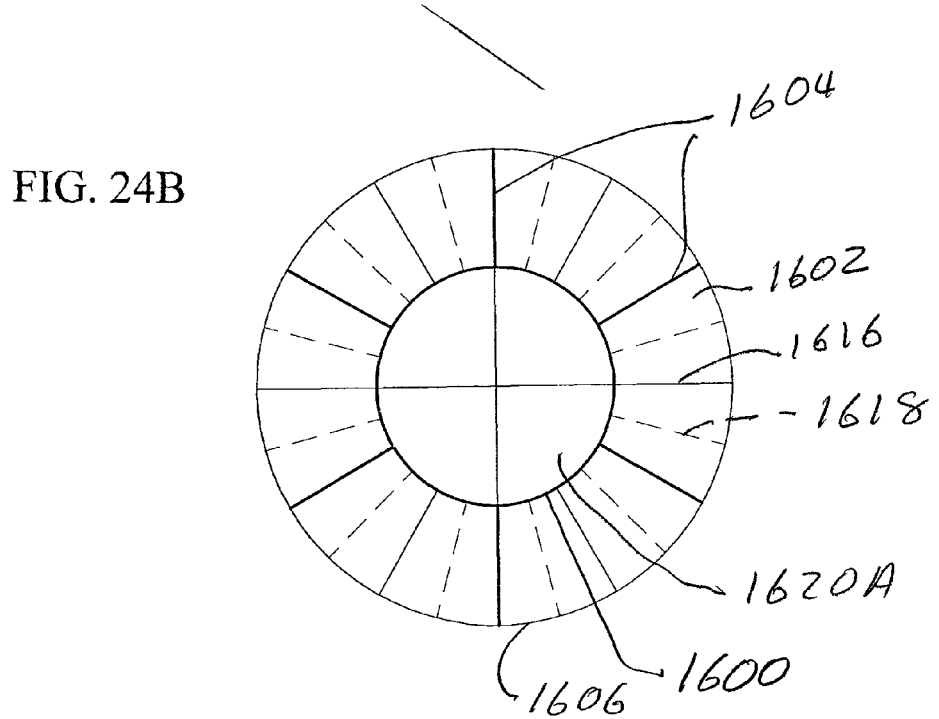
FIG. 24B is an inlet end view of the air flow device of FIG. 24A.
Figure 24C:
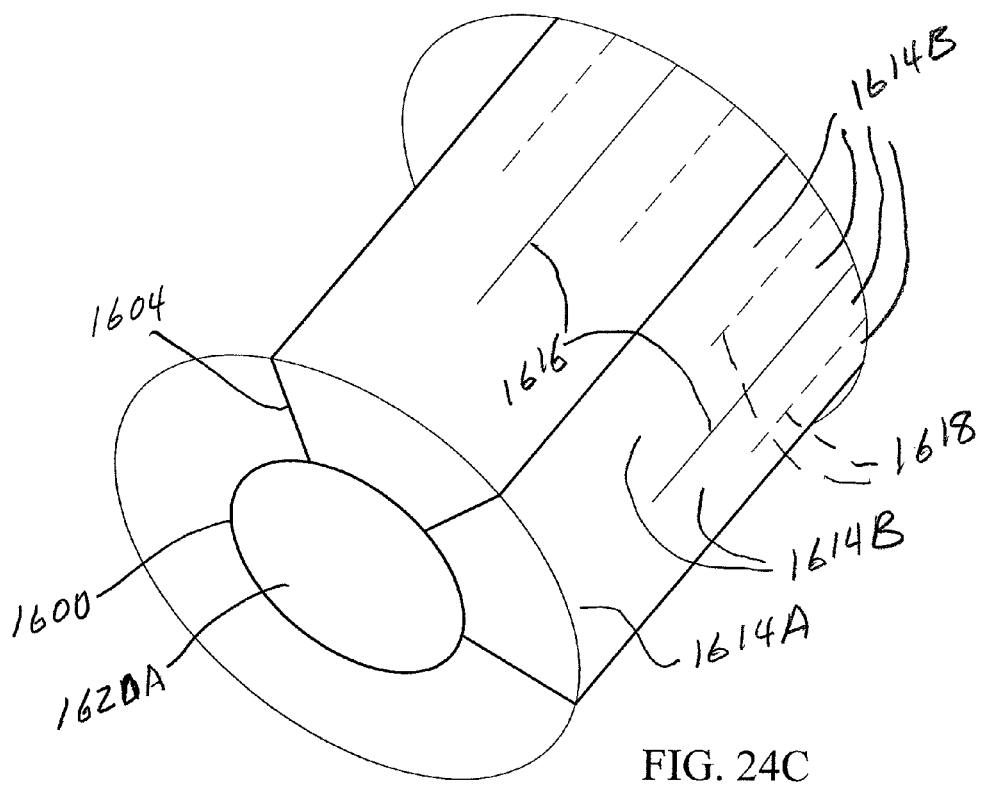
FIG. 24C is a schematic perspective view of a portion of air flow device of FIG. 24A.

FIGS. 24A, 24B, and 24C show an embodiment of the air flow device of the invention wherein the smaller tubes are not all cylindrical. As shown in FIGS. 24A, 24B, and 24C, a central inner tube 1600 is cylindrical with a circular cross sectional area S1. A surrounding second layer of inner tubes 1602 is created by equally dividing the space around the central tube with radially directed walls 1604 to form the second layer of inner tubes 1602 along the length of the inner tube, each of the tubes 1602 of the second layer having equal cross sectional areas S2. The outer walls of the second layer of inner tubes may be form by the outer tube 1606 which surrounds the cluster of inner tubes 1600 and 1602.

With this construction, all inner tubes 1600 and 1602 will have the same length and it will generally be desired that all will also have the same volume. Since all of the inner tubes will have the same length, for all their volumes to be equal, their cross sectional areas, S1 for cylindrical tube 1600 and S2 for non cylindrical tubes 1602, have to be equal as well, i.e., S1=S2. Depending on the number of tubes in the second layer, which can be any number n=1, 2, 3, . . . etc. (in this particular embodiment n=6), the cross sectional area S1 of the central inner tube 1600 can be calculated by dividing the cross sectional area S of the larger tube 1604 by (n+1)

$$S1=S/(n+1)$$

Since $S1=pi*R1^2$, and $S=pi*R^2$ (R is the radius of the cross section of larger tube 1604 and R1 is the radius of the inner cylindrical tube 1600), Then $$R1^2=R^2/(n+1) \rightarrow R1=R/(n+1)^{1/2}$$

In this particular case (n=6) R1 would be equal to the radius R of the larger tube divided by square root of 7.

If n=8 is chosen, then R1 would be equal to one third of R.

As shown in FIG. 24A, outer tube 1606 forming the spacer includes an inlet end 1608 with a single passage 1610 forming an inlet flow passage portion 1612. Each of the second layer inner tubes 1602 as shown in FIGS. 24B and 24C will include an initial single inlet passage 1614A and will include sequential radial dividers 1616 dividing the initial single passage 1614A into two equal sub flow passages 1614B and 1618 dividing each of the divided sub flow passages 1614B into two further divided sub flow passages 1614C. Central inner tube 1600 includes initial single inlet flow passage 1620A and will include sequential dividers, not shown, but which can be concentric dividers similar to the arrangement of the concentric dividers 462A and 462B in FIG. 8 to divide flow through inlet passage 1620A into two sub flow passages and then to divide the divided sub flow passages into additional sub flow passages. However, other divider arrangements can be used to divide the flow passage 1620A into additional equal sub flow passages.

As can be seen from the various illustrated embodiments of the invention, the various tubes and passages do not have to be cylindrical or all of the same size or length. However, as is apparent from the illustrations, for each flow passage or sub flow passage formed, the total cross sectional area is kept substantially the same along its entire length regardless of the subdivisions along the length. Thus, for example, when an inlet flow passage is formed, such as the inlet flow passage 30 of FIGS. 1-5, the total cross sectional area of the flow passage is substantially maintained through the device. This means that when the passage is divided into smaller sub flow passages, the total area of all such smaller sub flow passages at any point along the passage is substantially equal to the cross sectional area of the flow passage 30.

Figure 25:
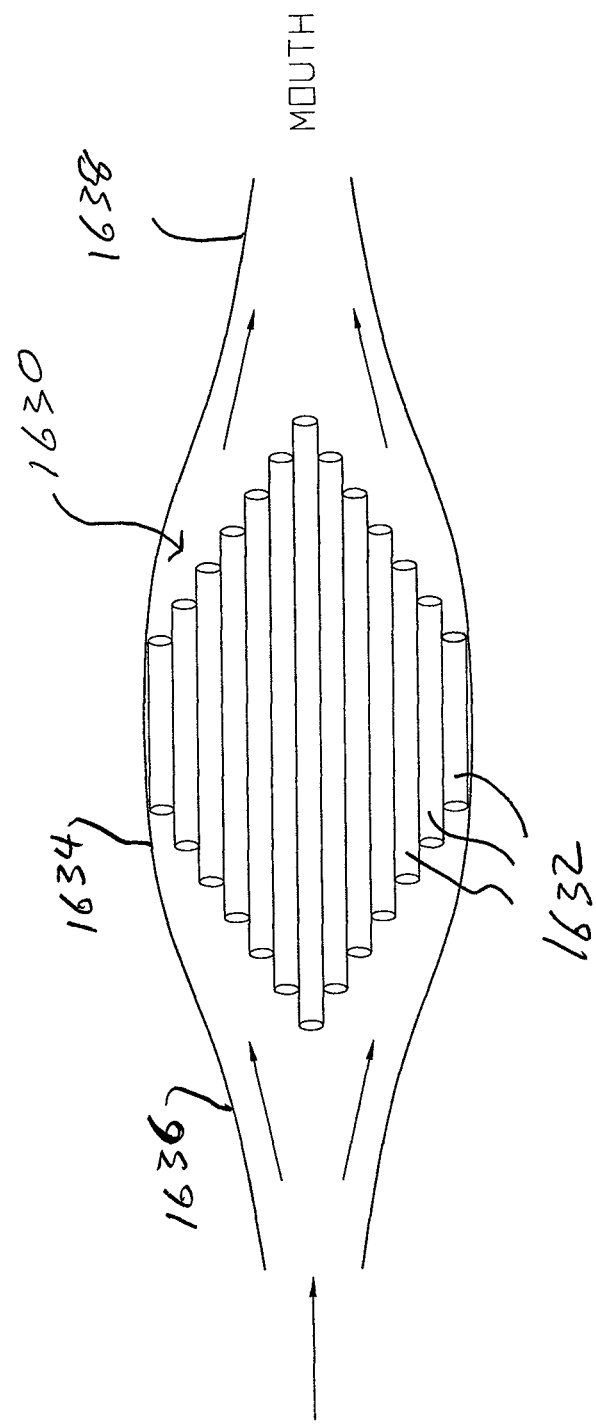
FIG. 25 is a side view of a further embodiment of an air flow device using a parallel cluster of basic air flow devices.

FIG. 25 shows a device of the invention usable as a spacer device showing a cluster 1630 of different length inner tubes 1632 with the larger outer tube 1634 having tapered ends to provide a smaller diameter tube both upstream and downstream of the cluster 1630. The upstream end 1636 of outer tube 1634 can provide the inlet end adapted to receive the outlet end 12 of the medication dispenser 10 and the downstream end 1638 of outer tube 1634 can provide the adapter 14 and mouthpiece 16 which is sized and shaped to fit into the mouth of a patient, all as shown in FIGS. 1, 4, and 5. It should be noted for this particular embodiment, that while the outer tube 1636 does not provide a complete flow passage therethrough of constant cross sectional area, the inner tubes 1632 all provide flow passages of substantially constant cross sectional area, and the outer tube 1636 merely adapts the laminar flow of fluid and particle suspension in the fluid created by the flow device formed by the inner tubes 1632 to the required input and output configurations and sizes.

The present invention also provides for a method for providing and maintaining laminar flow of a fluid and maintaining particle suspension in the fluid as the fluid flows along a fluid passage including sequentially dividing the flow of fluid in the passage into multiple smaller flows of fluid as the fluid flows along the passage from an inlet portion to an intermediate portion. Additionally, the flow of fluid in the passage can be sequentially divided into smaller flows of fluid as the fluid flows along the passage from intermediate portion to any additional intermediate portion or portions and from intermediate portion to an outlet portion.

The dividers of the air flow device of the present invention provide several advantages to fluid flow of aerosolized inhalable medicine. For example, it is believed the divider structure in the air passage of the air flow device aligns and guides the aerosolized medicine into the patient's airway, thereby reducing wasted medicine that may contact the sidewalls of traditional spacers. Additionally, it is believed the dividers reduce the turbulence and resistance of fluid flow through the spacer which also results in better medicine delivery. Moreover, the dividers significantly increase the surface area of the lateral walls, which serves to filter out lateral flow through the air passage. In this way, particles of aerosolized medicine that may become stuck on the lateral walls of the patient's airway are eliminated from the flow before they get to the patient's airway. Thus, the embodiments of the air flow devices described herein, provide better and more controlled delivery of the aerosolized medicine to a patient's lungs.

The concepts of the present invention described herein is not limited to use as a spacer for aerosol medicine applicators, but can be used anytime a fluid flows from one point to another point. For example, the dividers 60 of the air flow device 20 can be used to align and guide fluid within the space of an oxygen mask, endotracheal tube, nasal cannulas, and the like, or can be used in various other types of fluid flow passages, pipes, conduits, etc. Additionally, it will be appreciated that the sets of dividers 60 can be positioned or placed within a confined space, such as the cylindrical tube 32 described above, or the dividers 60 can be formed without an external wall such that the dividers can be placed within any existing fluid flow device or structure. In this way, the dividers can be used to improve or enhance various existing air flow passages, and are not limited to existing inhaler spacers.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

The invention claimed is:

1. A device for providing and maintaining laminar flow of a fluid and maintaining particle suspension in the fluid during fluid flow, comprising:
   a) a flow passage having opposite ends, said flow passage being divided into a plurality of connected sequential flow passage portions between the ends, the sequential flow passage portions including:
      i) an inlet flow passage portion extending into the flow passage from an inlet end;
      ii) an outlet flow passage portion disposed at the opposite end of the flow passage from the inlet flow passage portion; and
      iii) at least one intermediate flow passage passage portion between the inlet flow passage portion and the outlet flow passage portion;
      each flow passage portion other than the outlet flow passage portion having a next sequential flow passage portion and each flow passage portion other than the inlet flow passage portion having a next preceding flow passage portion;
   b) a plurality of divider sets, each divider set positioned in a different sequential flow passage portion of the flow passage to divide that flow passage portion into a predetermined number of sub flow passages, the number of sub flow passages in a next sequential flow passage portion being greater than the number of sub flow passages in the next preceding flow passage portion and each sub flow passage in a next sequential flow passage portion being in flow communication with only a single sub flow passage of the next preceding flow passage portion;
   c) whereby the flow passage is sequentially divided into an increasing number of the sub flow passages progressing from the inlet portion of the flow passage to the outlet portion of the flow passage and at least one of the sub flow passages of each sequential portion of the flow passage beyond the inlet flow passage portion is divided into a plurality of additional smaller sub flow passages in the next sequential flow passage portion of the flow passage.

2. A device for providing and maintaining laminar flow of a fluid and maintaining particle suspension in the fluid during fluid flow according to claim 1, wherein structure defining the flow passage is substantially cylindrical.

3. A device for providing and maintaining laminar flow of a fluid and maintaining particle suspension in the fluid during fluid flow according to claim 2, wherein when each sub flow passage from a next preceding flow passage portion is directly divided into connected additional sub flow passages in the next sequential flow passage portion, the sub flow passage from a next preceding flow passage portion is directly divided in half into two smaller connected additional sub flow passages in the next sequential flow passage portion.

4. A device for providing and maintaining laminar flow of a fluid and maintaining particle suspension in the fluid during fluid flow according to claim 3, wherein the inlet flow passage portion forms a single flow passage therein.

5. A device for providing and maintaining laminar flow of a fluid and maintaining particle suspension in the fluid during fluid flow according to claim 4, wherein each flow passage portion provides a total flow passage cross sectional area, and wherein the total flow passage cross sectional area of each flow passage portion is approximately equal.

6. A device for providing and maintaining laminar flow of a fluid and maintaining particle suspension in the fluid during fluid flow according to claim 5, wherein the device forms a spacer structure for an inhaler device for delivery of medication to a patient, wherein the inlet end is adapted to receive the outlet of a medication dispenser, and the outlet end is adapted to communicate with an air inlet of a patient.

7. A device for providing and maintaining laminar flow of fluid and maintaining particle suspension in the fluid during fluid flow according to claim 6, wherein the inlet end of the flow passage, in addition to being adapted to receive the outlet of a medication dispenser, includes an opening to allow atmospheric air flow into the inlet end of the flow passage.

8. A device for providing and maintaining laminar flow of a fluid and maintaining particle suspension in the fluid during fluid flow according to claim 7, wherein the outlet end is configured to attach to a mouthpiece to communicate with the mouth of a patient.

9. A device for providing and maintaining laminar flow of a fluid and maintaining particle suspension in the fluid during fluid flow according to claim 1, wherein the inlet end is adapted to receive the outlet of a pressurized metered dose inhaler.

10. A device for providing and maintaining laminar flow of a fluid and maintaining particle suspension in the fluid during fluid flow according to claim 1, wherein each flow passage portion provides a total flow passage cross sectional area, and wherein the total flow passage cross sectional area of each flow passage portion is approximately equal.

11. A device for providing and maintaining laminar flow of a fluid and maintaining particle suspension in the fluid during fluid flow according to claim 1, wherein the device forms a spacer structure for an inhaler device for delivery of medication to a patient, wherein the inlet end is adapted to receive the outlet of a medication dispenser, and the outlet end is adapted to communicate with an air inlet of a patient.

12. A device for providing and maintaining laminar flow of fluid and maintaining particle suspension in the fluid during fluid flow according to claim 11, wherein the inlet end of the flow passage, in addition to being adapted to receive the outlet of a medication dispenser, includes an opening to allow atmospheric air flow into the inlet end of the flow passage.

13. A device for providing and maintaining laminar flow of a fluid and maintaining particle suspension in the fluid during fluid flow, comprising:
   structure forming a flow passage having an inlet end and an outlet end; and
   a plurality of devices according to claim 1 clustered in parallel within the flow passage;
   whereby fluid flowing through the flow passage is divided into portions with different portions of the fluid flowing in parallel through respective different devices of the clustered plurality of devices according to claim 1.

14. A device for providing and maintaining laminar flow of a fluid and maintaining particle suspension in the fluid during fluid flow according to claim 13, wherein the plurality of devices according to claim 1 substantially fill a cross section of the flow passage whereby substantially all of the fluid flowing through the flow passage flows through a respective one of the different devices of the clustered plurality of devices according to claim 1.

15. A device for providing and maintaining laminar flow of a fluid and maintaining particle suspension in the fluid during fluid flow according to claim 14, wherein the flow passage is substantially cylindrical.

16. A device for providing and maintaining laminar flow of a fluid and maintaining particle suspension in the fluid during fluid flow according to claim 14, wherein the A plurality of devices according to claim 1 include devices of different lengths.

17. A device for providing and maintaining laminar flow of a fluid and maintaining particle suspension in the fluid during fluid flow according to claim 14, wherein the A plurality of devices according to claim 1 include such devices having different diameters.

18. A device for providing and maintaining laminar flow of a fluid and maintaining particle suspension in the fluid during fluid flow according to claim 13, wherein the A plurality of devices according to claim 1 do not fill a cross section of the flow passage.

19. A device for providing and maintaining laminar flow of a fluid and maintaining particle suspension in the fluid during fluid flow, comprising:
   a) a flow passage having opposite ends, said flow passage being divided into a plurality of connected sequential flow passage portions between the ends, the sequential flow passage portions including:
      i) an inlet flow passage portion extending into the flow passage from an inlet end;
      ii) an outlet flow passage portion disposed at the opposite end of the flow passage from the inlet flow passage portion; and
      iii) at least one intermediate flow passage portion between the inlet flow passage portion and the outlet flow passage portion;
      each flow passage portion other than the outlet flow passage portion having a next sequential flow passage portion and each flow passage portion other than the inlet flow passage portion having a next preceding flow passage portion;
   b) a plurality of divider sets, each divider set positioned in a different sequential flow passage portion of the flow passage to divide that flow passage portion into a predetermined number of sub flow passages, the number of sub flow passages in a next sequential flow passage portion being greater than the number of sub flow passages in the next preceding flow passage portion and each sub flow passage in a next sequential flow passage portion being in flow communication with only a single sub flow passage of the next preceding flow passage portion;

c) whereby a sub flow passage from a next preceding flow passage portion is directly divided into connected additional sub flow passages in the next sequential flow passage portion so that the flow passage is sequentially divided into an increasing number of sub flow passages in each flow passage portion progressing from the inlet end of the passage to the outlet end of the passage.

* * * * *